(12) United States Patent
Bar-Or et al.

(10) Patent No.: US 8,513,196 B2
(45) Date of Patent: *Aug. 20, 2013

(54) TREATMENT OF T-CELL MEDIATED DISEASES

(71) Applicant: DMI Biosciences, Inc., Greenwood Village, CO (US)

(72) Inventors: David Bar-Or, Englewood, CO (US); Raphael Bar-Or, Denver, CO (US); Richard Shimonkevitz, Larkspur, CO (US)

(73) Assignee: DMI Acquisition Corp., Greenwood Village, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/676,984

(22) Filed: Nov. 14, 2012

(65) Prior Publication Data

US 2013/0071436 A1 Mar. 21, 2013

Related U.S. Application Data

(63) Continuation of application No. 12/753,671, filed on Apr. 2, 2010, which is a continuation of application No. 10/846,482, filed on May 14, 2004, now Pat. No. 7,732,403.

(60) Provisional application No. 60/471,017, filed on May 15, 2003, provisional application No. 60/489,270, filed on Jul. 21, 2003, provisional application No. 60/514,930, filed on Oct. 27, 2003, provisional application No. 60/517,338, filed on Nov. 4, 2003.

(51) Int. Cl.
*A61K 38/05* (2006.01)
*A61K 38/12* (2006.01)

(52) U.S. Cl.
USPC ...... 514/17.7; 514/17.9; 514/21.1; 514/21.91

(58) Field of Classification Search
None
See application file for complete search history.

(56) References Cited

U.S. PATENT DOCUMENTS

| | | |
|---|---|---|
| 3,928,330 A | 12/1975 | Ramey et al. |
| 3,941,790 A | 3/1976 | Creighton |
| 3,976,773 A | 8/1976 | Curran |
| 4,006,261 A | 2/1977 | Pickenhagen et al. |
| 4,088,649 A | 5/1978 | Smith et al. |
| 4,205,057 A | 5/1980 | Whitaker |
| 4,289,759 A | 9/1981 | Heavner et al. |
| 4,312,987 A | 1/1982 | Beck |
| 4,331,595 A | 5/1982 | Heavner et al. |
| 4,661,500 A | 4/1987 | Rozencwaig |
| 4,694,061 A | 9/1987 | Pfeifer |
| 4,694,081 A | 9/1987 | Miller et al. |
| 4,771,056 A | 9/1988 | Rozencwaig |
| 4,806,538 A | 2/1989 | Shimazaki et al. |
| 4,886,796 A | 12/1989 | Eichner et al. |
| 4,940,709 A | 7/1990 | Shimazaki et al. |
| 4,992,552 A | 2/1991 | Hubbs et al. |
| 5,047,401 A | 9/1991 | Lipsky et al. |
| 5,144,073 A | 9/1992 | Hubbs |
| 5,238,938 A | 8/1993 | Tone et al. |
| 5,358,938 A | 10/1994 | Cai et al. |
| 5,418,218 A | 5/1995 | Wilber |
| 5,434,151 A | 7/1995 | Cai et al. |
| 5,463,083 A | 10/1995 | Biftu et al. |
| 5,503,852 A | 4/1996 | Steiner et al. |
| 5,512,544 A | 4/1996 | Wallach et al. |
| 5,538,993 A | 7/1996 | Mechoulam et al. |
| 5,543,402 A | 8/1996 | Bosies et al. |
| 5,543,503 A | 8/1996 | Chuntharapai et al. |
| 5,545,404 A | 8/1996 | Page |
| 5,550,132 A | 8/1996 | Benson et al. |
| 5,578,323 A | 11/1996 | Milstein et al. |
| 5,589,501 A | 12/1996 | Carrera et al. |
| 5,648,486 A | 7/1997 | Cai et al. |
| 5,693,338 A | 12/1997 | Milstein |
| 5,700,804 A | 12/1997 | Collins et al. |
| 5,703,093 A | 12/1997 | Cai et al. |
| 5,741,809 A | 4/1998 | Biftu et al. |
| 5,750,530 A | 5/1998 | Bryans et al. |
| 5,750,565 A | 5/1998 | Cai et al. |
| 5,776,892 A | 7/1998 | Counts et al. |
| 5,780,503 A | 7/1998 | Biftu et al. |
| 5,792,776 A | 8/1998 | Biftu et al. |

(Continued)

FOREIGN PATENT DOCUMENTS

| | | |
|---|---|---|
| CS | 254868 | 6/1987 |
| CZ | 2827.94 | 4/1996 |

(Continued)

OTHER PUBLICATIONS

Moss et al. ("Th1/Th2 cells in inflammatory disease states: therapeutic implications" Expert Opinion on Biological Therapy (2004) 4(12) 1887-1896.*
Sigma "Human Albumin" downloaded from www.sigmaaldrich.com on Jan. 8, 2013.*
Amersham Biosciences "Desalting and buffer exchange with Sephadex G-25" downlaoded from www.gelifesciences.com on Jan. 8, 2013.*
"Disposable PD-10 Desalting Columns," GE Healthcare Life Sciences, downloaded Nov. 1, 2011, 2 pages.
"Tryprostatin A, *Aspergillus fumigates*," available at www.emdbiosciences.com/Products/ProductDisplay.asp?catno=649305&, printed on Jun. 21, 2006, 1 page.

(Continued)

*Primary Examiner* — Christina Bradley
(74) *Attorney, Agent, or Firm* — Sheridan Ross P.C.

(57) ABSTRACT

The invention provides a method of treating T-cell mediated diseases and a method of inhibiting the activation of T-cells using certain diketopiperazines. The invention also provides methods of synthesizing diketopiperazines and pharmaceutical compositions comprising certain diketopiperazines. The invention further provides methods of making improved pharmaceutical compositions of proteins and peptides by either increasing or decreasing the content of diketopiperazines in the compositions and the resultant improved pharmaceutical compositions.

25 Claims, 5 Drawing Sheets

(56) References Cited

U.S. PATENT DOCUMENTS

| | | |
|---|---|---|
| 5,817,751 A | 10/1998 | Szardenings et al. |
| 5,834,032 A | 11/1998 | Song |
| 5,843,950 A | 12/1998 | Tasaka et al. |
| 5,856,323 A | 1/1999 | Cai et al. |
| 5,877,174 A | 3/1999 | Ono et al. |
| 5,883,227 A | 3/1999 | Kline et al. |
| 5,886,152 A | 3/1999 | Nakatani et al. |
| 5,902,812 A | 5/1999 | Brocchini et al. |
| 5,919,785 A | 7/1999 | Dinsmore et al. |
| 5,932,112 A | 8/1999 | Browning, Jr. |
| 5,932,579 A | 8/1999 | Campbell et al. |
| 5,976,569 A | 11/1999 | Milstein |
| 5,985,581 A | 11/1999 | Nixon et al. |
| 5,990,112 A | 11/1999 | Campbell et al. |
| 6,034,057 A | 3/2000 | Dutta |
| 6,034,221 A | 3/2000 | Berezenko et al. |
| 6,060,452 A | 5/2000 | Green et al. |
| 6,090,780 A | 7/2000 | Prasad |
| 6,096,737 A | 8/2000 | Loder |
| 6,099,856 A | 8/2000 | Milstein et al. |
| 6,107,050 A | 8/2000 | Alkon et al. |
| 6,180,616 B1 | 1/2001 | Fukunaga |
| 6,222,029 B1 | 4/2001 | Edwards et al. |
| 6,248,363 B1 | 6/2001 | Patel et al. |
| 6,262,119 B1 | 7/2001 | Ferrante et al. |
| 6,265,535 B1 | 7/2001 | Greene et al. |
| 6,331,318 B1 | 12/2001 | Milstein et al. |
| 6,358,957 B1 | 3/2002 | Fukumoto et al. |
| 6,395,774 B1 | 5/2002 | Milstein |
| 6,441,172 B1 | 8/2002 | Nefzi et al. |
| 6,461,875 B1 | 10/2002 | Bar-Or et al. |
| 6,475,743 B1 | 11/2002 | Bar-Or et al. |
| 6,492,179 B1 | 12/2002 | Bar-Or et al. |
| 6,531,505 B2 | 3/2003 | Xu et al. |
| 6,541,224 B2 | 4/2003 | Yu et al. |
| 6,555,543 B2 | 4/2003 | Bar-Or et al. |
| 6,635,649 B2 | 10/2003 | Teng et al. |
| 6,677,473 B1 | 1/2004 | Madison et al. |
| 6,689,765 B2 | 2/2004 | Baroudy et al. |
| 6,815,214 B2 | 11/2004 | Boyce et al. |
| 6,930,112 B2 | 8/2005 | Weaver et al. |
| 6,967,202 B2 | 11/2005 | Rao et al. |
| 7,026,322 B2 | 4/2006 | Hayashi et al. |
| 7,175,844 B2 | 2/2007 | King |
| 7,276,534 B2 | 10/2007 | Milstein |
| 7,288,545 B2 | 10/2007 | Teng et al. |
| 7,332,153 B2 | 2/2008 | Bhatia et al. |
| 7,378,403 B2 | 5/2008 | Kozikowski et al. |
| 7,575,929 B2 | 8/2009 | Bar-Or et al. |
| 7,732,403 B2 | 6/2010 | Bar-Or et al. |
| 7,919,497 B2 | 4/2011 | Palladino et al. |
| 8,030,488 B2 | 10/2011 | Sviridov et al. |
| 8,067,425 B2 | 11/2011 | Brimble et al. |
| 8,183,209 B2 | 5/2012 | Bar-Or et al. |
| 8,217,047 B2 | 7/2012 | Bar-Or |
| 8,268,830 B2 | 9/2012 | Bar-Or et al. |
| 2003/0119750 A1 | 6/2003 | Demuth et al. |
| 2003/0153575 A1 | 8/2003 | Orme et al. |
| 2003/0157030 A1 | 8/2003 | Davis et al. |
| 2003/0187226 A1 | 10/2003 | Goodey et al. |
| 2003/0203915 A1 | 10/2003 | Fang et al. |
| 2003/0225103 A1 | 12/2003 | Bar-Or et al. |
| 2004/0024180 A1 | 2/2004 | Drauz et al. |
| 2004/0038865 A1 | 2/2004 | Gelber et al. |
| 2004/0063654 A1 | 4/2004 | Davis et al. |
| 2005/0096323 A1 | 5/2005 | Cheng et al. |
| 2005/0249681 A1 | 11/2005 | Heidenfelder et al. |
| 2007/0060508 A1 | 3/2007 | Haberl et al. |
| 2007/0208087 A1 | 9/2007 | Sanders et al. |
| 2008/0017576 A1 | 1/2008 | Belfort et al. |
| 2008/0260838 A1 | 10/2008 | Hokenson et al. |
| 2010/0120056 A1 | 5/2010 | Bar-Or et al. |
| 2010/0143338 A1 | 6/2010 | Bar-Or et al. |
| 2010/0144611 A1 | 6/2010 | Bar-Or et al. |
| 2010/0190696 A1 | 7/2010 | Bar-Or et al. |
| 2012/0022003 A1 | 1/2012 | Bar-Or et al. |
| 2012/0022081 A1 | 1/2012 | Bar-Or et al. |
| 2012/0058934 A1 | 3/2012 | Bar-Or |
| 2012/0094918 A1 | 4/2012 | Bar-Or et al. |
| 2012/0157473 A1 | 6/2012 | Bar-Or |
| 2012/0172294 A1 | 7/2012 | Bar-Or |

FOREIGN PATENT DOCUMENTS

| | | |
|---|---|---|
| CZ | 280726 | 4/1996 |
| CZ | 2000-2680 | 7/2000 |
| CZ | 2000-2681 | 7/2000 |
| DE | 19937721 | 2/2001 |
| EP | 0043219 | 1/1982 |
| EP | 0214557 | 3/1987 |
| EP | 0216746 | 4/1987 |
| EP | 0220958 | 5/1987 |
| EP | 0493812 | 7/1992 |
| EP | 0557388 | 9/1993 |
| EP | 0610943 | 8/1994 |
| EP | 0655060 | 5/1995 |
| EP | 0835660 | 4/1998 |
| EP | 0939124 | 9/1999 |
| EP | 1445323 | 8/2004 |
| FR | 2717484 | 9/1995 |
| GB | 2263109 | 7/1993 |
| GB | 2372740 | 9/2002 |
| JP | 59-73574 | 4/1984 |
| JP | 61-112060 | 5/1986 |
| JP | 62-036331 | 2/1987 |
| JP | 63290868 | 11/1988 |
| JP | 01-013075 | 1/1989 |
| JP | 3176478 | 7/1991 |
| JP | 05-163148 | 6/1993 |
| JP | 07-247474 | 9/1995 |
| JP | 08-277203 | 10/1996 |
| JP | H08-277203 | 10/1996 |
| JP | 10-226615 | 8/1998 |
| JP | 10245315 | 9/1998 |
| JP | 11-504509 | 4/1999 |
| JP | 2000-327575 | 11/2000 |
| JP | 2002-527753 | 8/2002 |
| NZ | 218088 | 1/1989 |
| NZ | 335544 | 8/2001 |
| RU | 2112242 | 5/1998 |
| RU | 2125728 | 1/1999 |
| RU | 2128840 | 4/1999 |
| WO | WO 91/14378 | 10/1991 |
| WO | WO 93/08815 | 5/1993 |
| WO | WO 94/04512 | 3/1994 |
| WO | WO 94/04513 | 3/1994 |
| WO | WO 94/04537 | 3/1994 |
| WO | WO 94/20063 | 9/1994 |
| WO | WO 95/03054 | 2/1995 |
| WO | WO 95/18610 | 7/1995 |
| WO | WO 96/00212 | 1/1996 |
| WO | WO 96/00391 | 1/1996 |
| WO | WO 96/10396 | 4/1996 |
| WO | WO 96/32478 | 10/1996 |
| WO | WO 97/12625 | 4/1997 |
| WO | WO 97/36888 | 10/1997 |
| WO | WO 97/38011 | 10/1997 |
| WO | WO 97/48685 | 12/1997 |
| WO | WO 98/09968 | 3/1998 |
| WO | WO 98/40748 | 9/1998 |
| WO | WO 99/40931 | 8/1999 |
| WO | WO 99/49865 | 10/1999 |
| WO | WO 99/51256 | 10/1999 |
| WO | WO 99/51720 | 10/1999 |
| WO | WO 00/20454 | 4/2000 |
| WO | WO 00/20840 | 4/2000 |
| WO | WO 00/22439 | 4/2000 |
| WO | WO 00/43000 | 7/2000 |
| WO | WO 00/57187 | 9/2000 |
| WO | WO 01/34586 | 5/2001 |
| WO | WO 01/91713 | 12/2001 |
| WO | WO 02/11676 | 2/2002 |
| WO | WO 02/12201 | 2/2002 |
| WO | WO 02/059604 | 8/2002 |
| WO | WO 02/062797 | 8/2002 |

| | | |
|---|---|---|
| WO | WO 02/083667 | 10/2002 |
| WO | WO 02/089738 | 11/2002 |
| WO | WO 03/032809 | 4/2003 |
| WO | WO 03/045395 | 6/2003 |
| WO | WO 2004/034060 | 4/2004 |
| WO | WO 2004/048345 | 6/2004 |
| WO | WO 2004/054498 | 7/2004 |
| WO | WO 2004/103304 | 12/2004 |
| WO | WO 2005/011699 | 2/2005 |
| WO | WO 2009/042193 | 4/2009 |
| WO | WO 2012/033789 | 3/2012 |

OTHER PUBLICATIONS

Abraha et al., "C-terminal inhibition of tau assembly in vitro and in Alzheimer's disease," Journal of Cell Science, 2000, vol. 113, pp. 3737-3745.

Acharya et al., "Solid-phase synthesis of substituted imidazoline-tethered 2,3-diketopiperazines, cyclic ureas, and cyclic thioureas," J Comb Chem, Nov.-Dec. 2001, vol. 3(6), pp. 612-623.

Adorini, L., "Selective immunointervention in autoimmune diseases: lessons from multiple sclerosis," J Chemother, Jun. 2001, vol. 13(3), pp. 219-234 (Abstract Only Provided).

Akiyama et al., "Inflammation and Alzheimer's disease," Neurobiol Aging, 2000, vol. 21, pp. 383-421.

Alvarez et al., "Isolation and Structure Elucidation of Two New Calpain Inhibitors from *Streptomyces griseus*," J. Antibiotics, Nov. 1994, vol. 47(11), pp. 1195-1201.

Andreasen et al., "Cerebrospinal fluid beta-amyloid (1-42) in Alzheimer disease: differences between early- and late-onset Alzheimer disease and stability during the course of disease," Arch. Neurol., Jun. 1999, vol. 56(6), pp. 673-680.

Arbabi et al., "Priming Interleukin 8 Production: Role of Platelet-Activating Factor and p38," Arch Surg., Dec. 1999, vol. 134(12), pp. 1348-1353.

Ashwood et al. "Is autism an autoimmune disease?" Autoimmunity Reviews, Nov. 2004, vol. 3, No. 7-8, pp. 557-562.

Au et al., "Effect of PDE4 Inhibitors on Zymosan-Induced IL-8 Release From Human Neutrophils: Synergism with Prostanoids and Salbutamol," Br. J. Pharmacol, 1998, vol. 123, pp. 1260-1266.

Bagaria et al., "Cyclo(L-leucyl-alpha,beta-dehydrophenylalanine): the first diketopiperazine containing an alpha,beta-dehydrophenylalanine residue," Acta Crystallogr C., Mar. 2005, vol. 61(Pt 3), pp. 174-176, Epub Feb. 28, 2005.

Baig et al., "High Performance Liquid Chromatography as a Tool in the Definition of Abnormalities in Monamine and Tryptophan Metabolites in Cerebrospinal Fluid from Patients with Neurological Disorders," Biomed Chromatogr 1991, 5(3):108-112 (Abstract Only Provided).

Balk, "Lesson 24, vol. 12—ARDS: Pathophysiology of SIRS and MODS" www.chestnet.org/education/pccu/vol12/ lesson24.html, pp. 1-19, printed Jul. 20, 2000.

Banks et al., "Radioactively Iodinated Cyclo(His-Pro) Crosses the Blood-Brain Barrier and Reverses Ethanol-Induced Narcosis," Am J Physiol, May 1993, vol. 264(5 Pt. 1), pp. E723-E729 (Abstract Only Provided).

Bar-Or et al., "An Analog of the Human Albumin N-Terminus (Asp-Ala-His-Lys) Prevents Formation of Copper-Induced Reactive Oxygen Species," Biochemical and Biophysical Research Communications, 2001, vol. 284(3), pp. 856-862.

Bar-Or et al., "Potential Plasma Surrogate Biomakers for CNS Demyelinating Processes," 19th Congress of the European Committee for Treatment and Research in Multiple Sclerosis Meeting; Sep. 17-20, 2003; 2 pp. (Abstract first distributed at the meeting; attached is poster presented at meeting).

Barrow et al., WIN 64821, a New Competitive Antagonist to Substance P, Isolated from an *Aspergillus* Species: Structure Determination and Solution Conformation, J. Org. Chem., 1993, vol. 58, pp. 6016-6021.

Battersby et al., "Diketopiperazine Formation and N-Terminal Degradation in Recombinant Human Growth Hormone," Int. J. Pept. Protein Res, Sep. 1994, vol. 44(3), pp. 215-222 (Abstract Only Provided).

Berry et al., "Inhibition of Tau Polymerization by its Carboxy-Terminal Caspase Cleavage Fragment," Biochemistry, 2003, vol. 42, pp. 8325-8331.

Bhargava et al., "Inhibition of Neuroleptic-Induced Dopamine Receptor Supersensitivity by Cyclo (Leu-Gly)," Pharmacol Biochem Behav, Nov. 1980, vol. 13(5), pp. 633-636 (Abstract Only Provided).

Bhargava, "Antagonism of ketamine-induced anesthesia and hypothermia by thyrotropin releasing hormone and cyclo (His-Pro)," Neuropharmacology, 1981, vol. 20(7), pp. 699-702.

Bhargava, "Inhibition of abstinence syndrome in opiate dependent mice by cyclo (His-Pro)," Life Sci, 1981, vol. 28(11), pp. 1261-1267.

Bhargava, "The effect of melanotrophin release inhibiting factor (MIF) and cyclo (Leu-Gly) on the tolerance to morphine-induced antinociception in the rat: a dose-response study," Br J Pharmacol, Apr. 1981, vol. 72(4) (Abstract Only Provided).

Bhargava, "The effects of thyrotropin releasing hormone and histidyl-proline diketopiperazine on delta-9-tetrahydrocannabinol-induced hypothermia," Life Sci, 1980, vol. 26(11), pp. 845-850.

Bielekova et al., "Development of biomarkers in multiple sclerosis," Brain, Jul. 2004, vol. 127(Pt 7), pp. 1463-1478, Epub Jun. 4, 2004.

Binisti et al., "Structure-Activity Relationships in Platelet Activating Factor," J. Lipid Mediat. Cell Signal, Jan. 1997, vol. 15(2), pp. 125-144 (Abstract Only Provided).

Blazickova et al., "Immunomodulatory Characteristics of Synthetic Cyclic Dipeptides," Int. J. Immunotherapy, 1994, vol. 10(3), pp. 89-93.

Bowden et al., "Re-evaluation of histidyl-proline diketopiperazine [cyclo (His-Pro)] effects on food intake in the rate," Pharmacol. Biochem. Behav., Feb. 1988, vol. 29(2), pp. 357-363 (Abstract Only Provided).

Brauns et al., "Selected cyclic dipeptides inhibit cancer cell growth and induce apoptosis in HT-29 colon cancer cells," Anticancer Research, 2004, vol. 24, pp. 1713-1720.

Bressan et al., "Coordination chemistry of peptides. Part II. Crystal structure of cyclo-L-methionylglycine and studies of metal complexation," Int J Pept Protein Res, Apr. 1982, vol. 19(4) (Abstract Only Provided).

Bresser et al., "T-Cell Activation in the Lungs of Patients With Systemic Sclerosis and Its Relation With Pulmonary Fibrosis," Chest, Jul. 2001, 6 pages.

Bunn, "Early detection of lung cancer using serum RNA or DNA markers: ready for "prime time" or for validation?," J Clin Oncol., Nov. 1, 2003, vol. 21(21), pp. 3891-3893.

Caballero et al., "Brief synthesis of the cell cycle inhibitor tryprostatin B and its alanine analogue," Fourth International Electronic conference of Synthetic Organic Chemistry (ECXOC-4), Sep. 1-13, 2000, 4 pages, available at pages.unibas.ch/mdpi/eecxoc-4/c0023/c0023.htm.

Caballero et al., "Brief total synthesis of the cell cycle inhibitor tryprostatin B and related preparation of its alanine analogue," J Org Chem, Sep. 5, 2003, vol. 68(18) (Abstract Only Provided).

Carlton et al., "Attenuation of alcohol-induced hypothermia by cycle (His-Pro) and its analogs," Neuropeptides, Jun. 1995, vol. 28(6), pp. 351-355 (Abstract Only Provided).

Chan et al., "Site-Specific N-Terminal Auto-Degradation of Human Serum Albumin," Eur. J. Biochem., 1995, vol. 227, pp. 524-528.

Chen et al., "Up-regulation of Platelet-activating Factor Receptors in Lung and Alveolar Macrophages in the Bleomycin-Hamster Model of Pulmonary Fibrosis," J. Pharmacol. Exp. Ther., 1997, vol. 280(3), pp. 1219-1227.

Ciarkowski et al., "Conformation of cyclo-(D-phenylalanyl-trans-4-fluoro-D-prolyl)," Int. J. Pept. Protein Res., vol. 36, Sep. 1990, pp. 285-291.

Clark et al., "Roquefortine E, a Diketopiperazine from an Australian Isolate of *Gymnoascus reessii*," J. Nat. Prod., 2005, vol. 68(11), p. 1661-1664 (Abstract Only Provided).

Cody et al., "The design of potent and selective inhibitors of thrombin utilizing a piperazinedione template: part 2," Bioorg Med Chem Lett, Sep. 6, 1999, vol. 9(17), pp. 2503-2508.

Coggins et al., "High Affinity Specific Binding of the Thyrotrophin Releasing Hormone Metabolite Histidylproline to Rat Brain Membranes," Neuropeptides, Jan. 1987, vol. 9(1), pp. 83-91 (Abstract Only Provided).

Couladouros et al., "Solid-phase total synthesis of (−)-Phenylhistine and (−)-Aurantiamine. Synthesis of a diverse dehydro-2,5-diketopiperazine library. Part II," Mol Divers., 2005, vol. 9(1-3), pp. 111-121.

Crowe et al., "The N Terminal Region of Human Tau is Present in Alzheimer's Disease Protein A68 and is Incorporated into Paired Helical Filaments," American Journal of Pathology, 1991, vol. 139(6), pp. 1463-1470.

Cruse et al., "Illustrated Dictionary of Immunology" Second Edition, 2003, pp. 192, 260, 530-531.

Cui et al., "Novel Mammalian Cell Cycle Inhibitors, Tryprostatins A, B and Other Diketopiperazines Produced by *Aspergillus fumigatus* II. Physico-chemical properties and Structures," The Journal of Antibiotics, Jun. 1996, pp. 534-540.

Cytokines and Autoimmune Diseases, edited by Kuchroo, et al., 2002, Humana Press Inc., Totowa, NJ, pp. 3-23, 389-406.

Cytokines and Autoimmune Diseases, edited by Kuchroo, et al., 2002, Humana Press Inc., Totowa, NJ, pp. 5, 11, and 391.

Database WPI Section Ch, Week 199844 Derwent Publications Ltd., London, GB; AN 1998-515050 XP002369751 & JP 10 226615 A (Pola Chem Ind Inc) Aug. 25, 1998.

D'Alagni et al. "Effect of Urea on the Optical Rotatory Dispersion of Diketopiperazines of l-Serine, l-Alanine, l-Lysine, l-Valine, and l-Valylglycine." The Journal of Biological Chemistry, Nov. 10, 1969, vol. 244, No. 21, pp. 5843-5848.

Davidson et al., "Autoimmune Diseases," N. Engl. J. Med, 2001, vol. 345(5), pp. 340-350.

Degrassi et al., "Plant Growth-Promoting *Pseudomonas putida* WCS358 Produces and Secretes Four Cyclic Dipeptides: Cross-Talk with Quorum Sensing Bacterial Sensors," Current Microbiology, 2002, vol. 45, pp. 250-254.

Denault et al., "Transcriptional activation of the interleukin-8 gene by platelet-activating factor in human peripheral blood monocytes," Immunology, 1997, vol. 91, pp. 297-302.

Diamanti et al., "Distribution and Characterization of Cyclo (His-Pro)-like Immunoreactivity in the Human Gastrointestinal Tract," Neuropeptides, Mar. 1985, vol. 6(1):21-5 (Abstract Only Provided).

Dirr, K. et al., "The transformation of arginine into citrulline," Z. Physiol. Chem., 1935, vol. 237, pp. 121-130.

Duntas et al., "A Fast Protein Liquid Chromatography (FPLC) Method for Study of Thyrotropin-releasing Hormone (TRH) and its metabolite Histidyl-Proline Diketopiperazine (CHP) in Human Blood: Degradation in Liver and Pancreatic Diseases," Neuropeptides, 1993, vol. 25(6), pp. 357-361 (Abstract Only Provided).

Esposito et al., "The Solution Structure of the C-Terminal Segment of Tau Protein," Journal of Peptide Science, 2000, vol. 6, pp. 550-559.

Evans et al. "Metabolic effects of platelet-activating factor in rats in vivo: Stimulation of hepatic glycogenolysis and lipogenesis." Biochemical Journal, Jul. 1990, vol. 269, No. 1, pp. 269-272.

Faden et al., "Neuroprotective and nootropic actions of a novel cyclized dipeptide after controlled cortical impact injury in mice." J. Cerebral Blood Flow & Metabolism, 2003, vol. 23, pp. 355-363.

Faden et al., "Novel diketopiperazine enhances motor and cognitive recovery after traumatic brain injury in rats and shows neuroprotection in vitro and in vivo," J. Cerebral Blood Flow & Metabolism, 2003, vol. 23, pp. 342-354.

Faden et al., "Novel neuroprotective Tripeptides and Dipeptides," Ann. N.Y. Acad. Sci, 2005, vol. 1053, pp. 472-481.

Faden et al., "Novel small peptides with neuroprotective and nootropic properties," J. Alzheimer's Dis, 2004, vol. 6, pp. S93-S97.

Faden et al., "Novel TRH analog improves motor and cognitive recovery after traumatic brain injury in rodents," Am J Physiol, Oct. 1999, vol. 277(4 Pt 2), pp. R1196-R1204.

Fdhila et al., "dd-diketopiperazines: antibiotics active against *Vibrio anguillarum* isolated form marine bacteria associated with cultures of *Pecten maximus*" J Nat Prod, Oct. 2003, vol. 66(10) (Abstract Only Provided).

Fischer, "Diketopiperazines in Peptide and Combinatorial Chemistry," Journal of Peptide Science, 2003, vol. 9, pp. 9-35.

Folkes et al., "Synthesis and in vitro evaluation of a series of diketopiperazine inhibitors of plasminogen activator inhibitor-1," Bioorg Med Chem Lett, Oct. 2001, vol. 11(19), pp. 2589-2592 (Abstract Only Provided).

Fragner et al., "A New Biological Contribution of Cyclo(His-Pro) to the Peripheral Inhibition of Pancreatic Secretion," Am J Physiol, Dec. 1997, vol. 273(6 Pt. 1), pp. E1127-E1132 (Abstract Only Provided).

Gamblin et al., "Tau Polymerization: Role of the Amino Terminus," Biochemistry, 2003, vol. 42(7), pp. 2252-2257.

Garcia-Sierra et al., "Conformational Changes and Truncation of Tau Protein during Tangle Evolution in Alzheimer's Disease," Journal of Alzheimer's Disease, 2003, vol. 5, pp. 65-77.

Goolcharran et al., "Comparison of the Rates of Deamidation, Diketopiperazine Formation and Oxidation in Recombinant Human Vascular Endothelial Growth Factor and Model Peptides," AAPS PharmSci, 2000 vol. 2(1), p. E5 (Abstract Only Provided).

Gorbitz CH, "Crystal and Molecular Structure of cyclo-L-Aspartyl-L-alanyl (3,6-Dioxo-5-methyl-2-piperazineacetic acid)," Accession No. 1987:598911, Nov. 27, 1987, 1 page (Abstract).

Gorbitz, "Crystal and molecular structures of the isomeric dipeptides alpha-L-aspartyl-Lalanine and beta-L-aspartyl-L-alanine," Acta Chem Scand B., vol. 41(9), Oct. 1987, pp. 679-685.

Gorbitz "Crystal and Molecular Structure of cyclo-L-Aspartyl-L-alanyl (3,6-Dioxo-5-methyl-2-piperazineacetic acid)" Acta Chemica Scandinavica B, 1987, vol. 41, pp. 83-86.

Gordon et al, "Reductive Alkylation on a Solid Phase: Synthesis of a Piperazinedione Combinatorial Library," Bioorganic & Medicinal Chemistry Letters, 1995, vol. 5, No. 1, p. 47-50.

Gountopoulou et al. "TNFα is a potent inducer of platelet-activating factor synthesis in adipocytes but not in preadipocytes. Differential regulation by PI3K." Cytokine, Jan. 2008, vol. 41, No. 2 p. 174-181, (Abstract Only).

Graz et al "Cyclic Dipeptides in the Induction of Maturation for Cancer Therapy," J. Pharm. Pharmacol., 2000, vol. 52, pp. 75-82.

Graz et al., "Mechanism of a anti-fungal action of selected cyclic dipeptides," Pharmazie, Nov. 2001, vol. 56(11), pp. 900-901.

Gross et al., "Regulation of Interleukin-8 Production in a Human Colon Epithelial Cell Line (HT-29)," Gastroenterology, 1995, vol. 108, pp. 653-661.

Grubek-Jaworska et al., "CD4/CD8 lymphocytes in BALF during the efferent phase of lung delayed-type hypersensitivity reaction induced by single antigen inhalation," Med Sci Monit, Sep.-Oct. 2001, vol. 7(5), pp. 878-883 (Abstract Only Provided).

Gu et al., "Diketopiperazine Formation, Hydrolysis, and Epimerization of the New Dipeptide Angiotensin-Converting Enzyme Inhibitor RS-10085," Pharm Res, 1987, vol. 4(5), pp. 392-397 (Abstract Only Provided).

Gudasheva et al., "Anxiolytic activity of endogenous nootropic dipeptide cycloprolylglycine in elevated plus-maze test," Bull Exp Biol Med, May 2001, vol. 131(5) (Abstract Only Provided).

Gudasheva et al., "Identification of a novel endogenous memory facilitating cyclic dipeptide cyclo-prolylglycine in rat brain," FEBS Lett, Aug. 5, 1996, vol. 391(1-2) (Abstract Only Provided).

Guerra et al., "PEGylation Prevents the N-Terminal Degradation of Megakaryocyte Growth and Development Factor," Pharm Res, 1998, vol. 15(12), pp. 1822-1827 (Abstract Only Provided).

Gustafson, "Adipose Tissue, Inflammation and Atherosclerosis," J. Atheroscler. Thromb., Apr. 30, 2010, vol. 17(4), pp. 332-341.

Hansel et al. "Metabolic Syndrome Is Associated with Elevated Oxidative Stress and Dysfunctional Dense High-Density Lipoprotein Particles Displaying Impaired Antioxidative Activity." The Journal of Clinical Endocrinology & Metabolism, Oct. 2004, vol. 89, No. 10, pp. 4963-4971.

Hasegawa et al., "Protein Sequence and Mass Spectrometric Analysis of Tau in the Alzheimer's Disease Brain," Journal of Biological Chemistry, 1992, vol. 267(24), pp. 17047-17054.

Hayashi et al., "Synthetic Hexa- and Heptapeptides That Inhibit IL-8 from Binding to and Activating Human Blood Neutrophilsl," J. Immunol., 1995, vol. 154, pp. 814-824.

Hilton et al., "Food Contains the Bioactive Peptide, Cyclo(His-Pro)," J. Clin Endocrinol Metab, Aug. 1992, vol. 75(2), pp. 375-378 (Abstract Only Provided).

Hilton et al., "Identification and Characterization of Cyclo (His-Pro)-Like Immunoreactivity in Amniotic Fluid," Peptides, Mar.-Apr. 1989, vol. 10(2), pp. 299-301 (Abstract Only Provided).

Hilton et al., "Radioimmunoassay of Cyclo(His-Pro) in Unextracted Human Plasma: Report of a Normal Range and Definition of Factors Critical for Successful Assay," Neuropeptides, 1989, vol. 13(1), pp. 65-70 (Abstract Only Provided).

Hilton et al., "Relationship between Plasma Cyclo (His-Pro), a Neuropeptide Common to Processed Protein-Rich Food, C-Peptide/Insulin Molar Ratio in Obese Women," Nutr Neurosci, 2001, vol. 4(6), pp. 469-474 (Abstract Only Provided).

Hlinak et al., "Effect of alaptide, its analogues and oxiracetam on memory for an elevated plus-maze in mice," European Journal of Pharmacology, 1996, vol. 314, pp. 1-7.

Hoffman et al., "An Enzymatically Stable Peptide with activity in the Central Nervous System: Its Penetration through the Blood-CSF Barrier," Brain Res, Feb. 11, 1977, vol. 122(1), pp. 87-94 (Abstract Only Provided).

Holden et al., "Quorum-sensing cross talk: isolation and chemical characterization of cyclic dipeptides from *Pseudomonas aeruginosa* and other Gram-negative bacteria," Moleclur Microbiology, 1999, vol. 33(6), pp. 1254-1266.

Houston et al., "The cyclic dipeptide CI-4 [cyclo-(l-Arg-d-Pro)] inhibits family 18 chitinases by structural mimicry of a reaction intermediate," Biochem J., Nov. 15, 2002, vol. 368(Pt 1) (Abstract Only Provided).

Hwang et al., "Effects of cyclo (his-pro) plus zinc on glucose metabolism in genetically diabetic obse mice," Diabetes Obes. Metab., Sep. 2003, vol. 5(5), pp. 317-324 (Abstract Only Provided).

Iriuchijima et al., "Thyrotripin-Releasing Hormone and Cyclo (His-Pro)-Like Immunoreactivities in the Cerebrospinal Fluids of 'Normal' Infants and Adults, and Patients with Various Neuropsychiatric and Neurologic Disorders," Life Sci. 1987, 41(22):2419-2428, Abstract only, from PubMed—PMID:2891013.

Ishibashi et al., "A Mechanism for Bitter Taste Sensibility in Peptides," Agric. Biol. Chem., 1988, vol. 52(3), pp. 819-827.

Ishibashi et al., "Bitterness of Leucine-Containing Peptides," Agric. Biol. Chem., 1987, vol. 51(9), pp. 2389-2394.

Ishii, et al. "Incidence of brain tumors in rats fed aspartame," Toxicology Letters, 1981, vol. 7, pp. 433-437.

Jackson et al., "Amyotrophic Lateral Sclerosis: Thryrotropin-releasing hormone and histidyl proline diketopiperazine in the spinal cord and cerebrospinal fluid," Neurology, 1986, vol. 36(9), pp. 1218-1223.

Jamie et al., "The effect of the isomers of cyclo(Trp-Pro) on heart and ion-channel activity," J Pharm Pharmacol, Dec. 2002, vol. 54(12) (Abstract Only Provided).

Jara et al., "Elevated serum levels of cyclo (His-Pro), and endogenous inhibitor ofpituitary prolactin secretion, in systemic lupus erythematosus patients," Lupus, 1997, vol. 6(3) (Abstract Only Provided).

Jaspan et al., "Study of Passage of Peptides Across the Blood-Brain Barrier: Biological Effects of Cyclo(His-Pro) After Intravenous and Oral Administration," Annals of the New York Academy of Science, 1994, vol. 739, pp. 101-107 (Abstract Only Provided).

Jiang et al. "Asymmetric Reformastky reaction catalyzed by amino acid derivatives," Huaxue Tongbao CKNI, 2001, vol. 10, pp. 637-640 (English Abstract).

Jicha et al., "Sequence Requirements for Formation of Conformational Variants of Tau Similar to Those Found in Alzheimer's Disease," Journal of Neuroscience Research, 1999, vol. 55, pp. 713-723.

Kaakkola et al., "Effects of two diketopiperazines, cyclo (His-Pro) and cyclo (Asp-Phe), on striatal dopamine: A microdialysis study," Brain Research Bulletin, 1993, vol. 32(6), pp. 667-672.

Kanzaki et al., "Enzymatic synthesis of dehydro cyclo(His-Phe)s, analogs of the potent cell cycle inhibitor, dehydrophenylahistin, and their inhibitory activities toward cell division," Biosci Biotechnol Biochem, Nov. 2004, vol. 68(11), pp. 2341-2345 (Abstract Only Provided).

Kasperska-Zajac et al. "Platelet Activating Factor as a Mediator and Therapeutic Approach in Bronchial Asthma." Inflammation, Apr. 2008, vol. 31, No. 2, pp. 112-120.

Kikwai et al, "Stability and degradation profiles of Spantide II in aqueous solutions," Eur J Pharm Sci, Feb. 2006, vol. 27(2-3), pp. 158-166, Epub Nov. 2, 2005 (Abstract Only Provided).

Kilian et al., "Biological activity of selected tyrosine-containing 2,5-diketopiperazines," Pharmazie, Apr. 2005, vol. 60(4), pp. 305-309 (Abstract Only Provided).

Kilian et al., "The effect of the isomer of cyclo(Trp-Pro) on heart and ion-channel activity," J. Pharm. Pharmacol., Dec. 2002, vol. 54(12), pp. 1659-1665 (Abstract Only Provided).

Kobayashi et al., "Neuropeptide Y and histidyl-proline diketopiperazine," Rinsho-Kensa, Japan, Sep. 1987, vol. 21, No. 9, pp. 984-991.

Kopple et al. "Conformation of Cyclo-(l-Threonine)2 and Cyclo-(l-Allo Threonine)2 : A Proton and Carbon N.m.r. Study." International Journal of Peptide Protein Research, Jul. 1981, vol. 18, No. 1, pp. 33-40.

Koskinen, "Effect of Low Intravenous Doses of TRH, Acid-TRH and Cyclo (His-Pro) on Cerebral and Peripheral Blood Flows," British Journal of Pharmacology, 1986, vol. 87(3), pp. 509-519 (Abstract Only Provided).

Kow et al., "The Effects of the TRH Metabolite Cyclo(His-Pro) and Its Analogs on Feeding," Pharmacology, Biochemistry & Behavior, 1991, vol. 38, pp. 359-364.

Kuenz et al., "Plasma levels of soluble adhesion molecules sPECAM-1, sP-selectin and sE-selectin are associated with relapsing-remitting disease course of multiple sclerosis," J. Neuroimmunol, Oct. 2005, vol. 167(1-2), pp. 143-149.

Kulikov et al., "Review: The Bioregulatory Role of Platelet-Activating Factor in Intracellular Processes and Cell-Cell Interactions," 1997, www.protein.bio.msu.su/biokhimiya/contents/v63/full/63010057.html, pp. 1-13.

Kurahashi et al., "Histydyl-Proline Diketopiperazine (HPD), A Metabolite of Thyrotropin-Releasing Hormone (TRH), Improves the Ataxic Gait in 3-Acetylpyridine (3-AP) Treated Rats," No To Shinkei, Sep. 1986, vol. 38(9), pp. 893-898 (Abstract Only Provided).

Larsen et al. "Kinetics of degradation and oil solubility of ester prodrugs of a model dipeptide (Gly-Phe)," Eur J Pharm Sci, Aug. 2004, vol. 22(5), pp. 399-408 (Abstract Only Provided).

Lechan et al., "Thyrotropin Releasing Hormone but not Histidyl-Proline Diketopiperazine is Depleted from Rat Spinal Cord Following 5,7-Dihydroxytryptamine Treatment," Brain Research, 1985, vol. 326(1), pp. 152-155 (Abstract Only Provided).

Lechin et al., "Plasma Neurotransmitters and Cortisol in Chronic Illness: Role of Stress," J Medicine, 1994, vol. 25(3-4), pp. 181-192 (Abstract Only Provided).

Leduque et al., "Histidyl-Proline Diketopiperazine (His-Pro DKP) Immunoreactivity is Present in the Glucagon-Containing Cells of the Human Fetal Pancreas," J Clin Invest, 1987, 79(3):875-880 (Abstract Only Provided).

Lee et al., "Cyclo (Leu-Gly attenuates the striatal dopaminergic supersensitivity induced by chronic morphine," Alcohol Drugs Res, 1987, vol. 7(1) (Abstract Only Provided).

Lehninger et al., "Amino Acids and Peptides," Chapter 5 of Principles of Biochemistry, 1993, 2nd edition, pp. 111-133.

Lindner et al., "[Effects of cyclic adenosine-3',5'-monophosphate and cyclo{Lys-Pro}.HCl neuronotrophic factors in tissue culture]," J Hirnforsch, 1987, vol. 28(3) (Abstract Only Provided).

Liu et al., "Hydroxyprolylserine derivatives JBP923 and JBP485 exhibit the antihepatitis activities after gastrointestinal absorption in rats," J Pharmacol Exp Ther, Aug. 2000, vol. 294(2) (Abstract Only Provided).

Luca et al., "Determination of serotonin content and ceruloplasmin activity, of blood and CSF amino acid level in multiple sclerosis," Neurol Psychiatr (Bucur), 1986, vol. 24(3), pp. 153-159.

Lucietto et al., "The biological activity of the histidine-containing diketopiperazines cyclo (His-Ala) and cyclo (His-Gly)," Peptides, Nov. 2006, vol. 27(11), pp. 2706-2714, Epub Jun. 21, 2006 (Abstract Only Provided).

Mayer, "Immunology—Chapter Four," Immunoglobulins—Structure and Function, online at pathmicro.med.sc.edu/mayer/IgStruct2000.htm, University of South Carolina School of Medicine, Nov. 6, 2009, 8 pages.

Mazza et al., "Potential energy calculations on phenylalanine rotamers in different boat forms of proline-containing cyclic dipeptides," Int. J. Pept. Protein Res., vol. 31, Feb. 1988, pp. 157-163.

McCain et al., "Endorphinergic modulation of immune function: potent action of the dipeptide glycyl-L-glutamine," Life Science, 1987, vol. 41, pp. 169-176.

McCain et al., "Modulation of Human T-Cell Suppressor Activity by Beta Endorphin and Glycyl-L-Glutamine," Int. J. Immunopharmoc, 1986, vol. 8(4), pp. 443-446.

McCleland et al., "An investigation into the biological activity of the selected histidine-containing diketopieperazines cyclo(His-Phe) and cyclo(His-Tyr)," Journal of Pharmacy and Pharmacology, Sep. 2004, vol. 56(9), pp. 1143-1153.

Meester et al., "In Vivo Inhibition of Dipeptidyl Peptidase IV Activity by Pro-Pro-diphenyl-phosphonate (Prodipine)," Biochemical Pharmacology, 1997, vol. 54, pp. 173-179.

Mentlein et al., "Dipeptidyl-Peptidase IV Hydrolyses Gastric Inhibitory Polypeptide, Glucagon-Like Peptide-1(7-36)amide, Peptide Histidine Methionine and is Responsible for their Degradation in Human Serum," European Journal of Biochemistry, 1993, vol. 214(3), pp. 829-835 (Abstract Only Provided).

Mesh, "Autoimmune Diseases,"internet document <<www.ncbi.nlm.nih.gov/sites/entrez>>, accessed Oct. 31, 2007, 2 pages.

Michell et al., "Biomarkers and Parkinson's Disease," Brain, Aug. 2004, vol. 127, pp. 1693-1705.

Miller et al., "Peptide Inhibitor of Interleukin-8 (IL-8) Reduces Staphylococcal Enterotoxin-A (SEA) Induced Neutrophil Trafficking to the Lung," Inflamm. Res., 1996, vol. 45, pp. 393-397.

Milne, et al. "The biological activity of selected cyclic dipeptides," J. Pharm. Pharmacol., 1998, vol. 50, pp. 1331-1337.

Minelli et al., "Phosphoproteomic analysis of the effect of cyclo-[His-Pro] dipeptide on PC12 cells." Peptides, Jan. 2006;27(1):105-13. Epub Aug. 30, 2005, Abstract only PMID: 16137790.

Mitsuma et al., "Radioimmunoassay for Thyrotropin-Releasing Hormone Precursor Peptide, Lys-Arg-Gln-His-Pro-Gly-Arg-Arg," Exp Clin Endocrinology, 1989, vol. 93(1), pp. 53-60 (Abstract Only Provided).

Mizuma et al., "Concentration-Dependent Preferences of Absorptive and Excretive Transport Cause Atypical Intestinal Absorption of Cyclic Phenylalanylserine: Small Intestine Acts as an Interface Between the Body and Ingested Compounds," Research Communications in Molecular Pathology and Pharmacology, 2002, vol. 111, pp. 199-209.

Mizuma et al., "Intestinal Absorption of Stable Cyclic Glycylphenylalanine: Comparison with the Linear Form," J. Pharm. Pharmacol., 1997, vol. 49, pp. 1067-1071.

Molodavkin et al., "[Effect of the novel dipeptide nootropic agent noopept and its metabolite cyclo-L-prolylglycine on the transcallosal evoked potential in the rat brain]," Eksp Klin Farmakol, Mar.-Apr. 2002, vol. 65(2) (Abstract Only Provided).

Monaco et al., "Plasma and cerebrospinal fluid tryptophan in Multiple Sclerosis and Degenerative Diseases," J Neurol Neurosurg Psychiatry, 1979, vol. 42(7), pp. 640-641 (Abstract Only Provided).

Montine et al., "Cerebrospinal Fluid Ab42, Tau, and F2-Isoprostane Concentrations in Patients with Alzheimer Disease, Other Dementias, and in Age-Matched Controls," Acrch Pathol Lab. Med, Apr. 2001, vol. 125, pp. 510-512.

Mori et al.,"Alteration by Liquid Protein Diet of TRH and Cyclo(His-Pro) in the Young Rat Brain," Res. Commun Chem Pathol Pharmacol, 1985, vol. 47(1), pp. 157-160 (Abstract Only Provided).

Mori et al., "Brain TRH and Cyclo (His-Pro) and Brain Protein in the Newborn Rat are Altered by Maternal Liquid Protein Feeding," Life Sci, 1983, vol. 32(14), pp. 1607-1612 (Abstract Only Provided).

Mori et al., "Distribution of histidyl-proline diketopiperazine [cyclo (His-Pro)] and thyrotropin-releasing hormone (TRH) in the primate central nervous system," Brain Res, 1982, vol. 245(1), pp. 183-186.

Mori et al., "Histidyl-Proline Diketopiperazine Cyclo (His-Pro): Identification and Characterization in Rat Pancreatic Islets," Biochem Biophys Res Commun, 1983, vol. 115(1), pp. 281-286 (Abstract Only Provided).

Mori et al., "Histidyl-Proline Diketopiperazine cyclo (His-Pro): measurement by radioimmunoassay in human blood in normal subject and in patients with hyper- and hypothyroidism," Biochem Biophys Res Commun, 1982, vol. 109(2), pp. 541-547.

Mori et al., "Regional Dissociation of Histidyl-Proline Diketopiperazine (Cyclo-(His-Pro)) and Thyrotropin-Releasing Hormone (TRH) in the Rat Brain," Brain Research, 1982, vol. 231(2), pp. 451-453 (Abstract Only Provided).

Mori et al., "Specific Radioimmunoassay of Cyclo (His-Pro), a Biologically Active Metabolite of Thyrotropin-Releasing Hormone," Endocrinology, 1981, vol. 108(5), pp. 1995-1997 (Abstract Only Provided).

Mori et al., ["TRH and Cyclo (His-Pro) Concentrations in the Young Rat Brain are Altered by a Liquid Protein Diet]," [Article in Japanese], Nippon Naibunpi Gakkai Zasshi, 1987, vol. 63(7), pp. 846-852.

Morley et al., "Neuropeptides and appetite: contribution of neuropharmacological modeling," Fed. Proc., Nov. 1984, vol. 43(14), pp. 2903-2907 (Abstract Only Provided).

Moss et al., "Kinetics and Mechanism of the Facile Cyclization of Histidyl-Prolineamide to Cyclo (His-Pro) in Aqueous Solution and the Competitive Influence of Human Plasma," J Pharm Pharmacol, 1990, vol. 42(1), pp. 7-12 (Abstract Only Provided).

Murray et al., "Role of α-Synuclein Carboxy-Terminus on Fibril Formation in Vitro," Biochemistry, 2003, vol. 42, pp. 8530-8540.

Nicholson et al., "NPI-2358 is a tubulin-depolymerizing agent: in-vitro evidence for activity as a tumor vascular-disrupting agent," Anticancer Drugs, Jan. 2006, vol. 17(1), pp. 25-31 (Abstract Only Provided).

Nitecki et al., "A Simple Route to Sterically Pure Kiketopiperazines" J. Org. Chem., 1968, vol. 33(2), pp. 864-866.

Online Medical Dictionary definition of albumin, medical-dictionary.thefreedictionary.com/albumin, downloaded Nov. 1, 2011, 4 pages.

Ostrovskaia et al., "Multicomponent antithrombotic effect of the neuroprotective prolyl dipeptide GVS-111 and its major metabolite cyclo-L-prolylglycine," Eksp Klin Farmakol, Mar.-Apr. 2002, vol. 65(2) (Abstract Only Provided).

Palace et al. "Epilepsy: an autoimmune disease?" Journal of Neurology, Neurosurgery & Psychiatry, Dec. 2000, vol. 69, No. 6, pp. 711-714.

Palacios et al., "Tenidap Decreases IL-8 and Monocyte Chemotactic Peptide-1 (MCP-1) mRNA Expression in the Synovial Tissue of Rabbits with Antigen Arthritis and in Cultured Synovial Cells," Clin. Exp. Immunol., 1998, vol. 111, pp. 588-596.

Pandey et al., "Synthetic Peptides Corresponding to a Repetitive Sequence of Malarial Histidine Rich Protein Bind Haem and Inhibit Haemozoin Formation in vitro," Mol Biochem Parasitol, 1997, vol. 90(1), pp. 281-287 (Abstract Only Provided).

Parker et al., "Evidence for the Presence of Immunoreactive Histidyl-Proline Diketopiperazine [Cyclo (His-Pro)] in the Adult Human Brain," Peptides, Nov.-Dec. 1983, vol. 4(6), pp. 879-881 (Abstract Only Provided).

Pekary et al., "In vitro Production of a TRH-Homologous Peptide and His-Pro Diketopiperazine by Human Semen," J Androl, 1985, vol. 6(6), pp. 379-385 (Abstract Only Provided).

Prakash et al., "Synthesis and Biological Activity of Novel Neuroprotective Diketopiperazines," Bioorganic & Medicinal Chemistry, Sep. 2002, vol. 10(9), pp. 3043-3048.

Prasad et al., "Distribution and Characterization of Cyclo (His-Pro)-Like Immunoreactivity in Human Cerebrospinal Fluid," Biochem Biophys Res Commun, 1986, vol. 136(2), pp. 835-842 (Abstract Only Provided).

Prasad et al., "Distribution and Metabolism of Cyclo (His-Pro): A New Member of the Neuropeptide Family," Peptides, May-Jun. 1982, vol. 3(3), pp. 591-598 (Abstract Only Provided).

Prasad et al., "Increased cerebrospinal fluid cyclo(His-Pro) content in schizophrenia," Neuropeptides, Nov. 1991, vol. 20(3), pp. 187-190.

Prasad et al., "Isolation of cyclo(His-Pro)-like immunoreactivity from Human Urine and Demonstration of its Immunologic, Pharmacologic, and Physico-chemical Identity with the Synthetic Peptide," Biochemistry Int, 1990, vol. 21(3), pp. 425-434 (Abstract Only Provided).

Prasad et al., "Thermoregulation in rats: opposing effects of thyrotropin releasing hormone and its metabolite histidyl-proline diketopiperazine," Biochem Biophys Res. Commun., 1978, vol. 85(4), pp. 1582-187.

Prasad, "Bioactive Cyclic Dipeptides," Peptides, 1995, vol. 16(1), pp. 151-164.

Purves et al. (Eds), Neuroscience, 2001, Sinauer Associates, Inc., 2nd Edition, pp. 75, 367, 400 and 403.

Purves et al., Life: the Science of Biology, 3rd Ed. (1992), p. 376.

Rainbow et al., "Distribution, survival and biological effects in mice of a behaviorally active, enzymatically stable peptide: pharmacokinetics of cyclo(Leu-Gly) and puromycin-induced amnesia," Pharmacol Biochem Behav, May 1979, vol. 10(5), pp. 787-793.

Rainger et al., "Endothelial-Borne Platelet-Activating Factor and Interleukin-8 Rapidly Immobilize Rolling Neutrophils," Am. J. Physiol., 272(Heart Circ. Physiol. 41):H114-H122 (1997).

Rainsford et al., "Effects of 5-Lipoxygenase Inhibitors on Interleukin Production by Human Synovial Tissues in Organ Culture: Comparison with Interleukin-1-Synthesis Inhibitors," J. Pharm. Pharmacol., 48:46-52 (1996).

Reubsaet et al., "Qualitative and Quantitative Aspects of the Degradation of Several Tripeptides Derived from the Antitumor Peptide Antagonist [Arg(6), D-Trp(7,9), MePhe(8)] Substance P[6-11]," J Pharm Biomed Anal 1999, 19(3-4):2.

Rinaldi et al. "Immunological markers in multiple sclerosis: tackiling the missing elements," Neurol. Sci., Dec. 2005, vol. 26 Suppl. 4, pp. S215-S217.

Rosenthal et al., "Effects of Arachidonic Acid and Cyclo (His-Pro) on Zinc Transport Across Small Intestine and Muscle Tissues," Life Sci, 2001, vol. 70(3), pp. 337-348 (Abstract Only Provided).

Roth et al., "Platelet-Activating Factor Exerts Mitogenic Activity and Stimulates Expression of Interleukin 6 and Interleukin 8 in Human Lung Fibroblasts via Binding to its Functional Receptor," J. Exp. Med., 1996, vol. 184, pp. 191-201.

Sakurada et al., "Antinociceptive activities of synthetic dipeptides in mice." J. Pharm. Pharmacol., 1982, vol. 34, pp. 750-751.

Sakuta et al., "Dual Regulatory Effects of Interferon-$\alpha$, -$\beta$, and -$\gamma$ on Interleukin-8 Gene Expression by Human Gingival Fibroblasts in Culture Upon Stimulation with Lipopolysaccharide from *Prevotella intermedia*, Interleukin-1$\alpha$, or Tumor Necrosis Factor-$\alpha$," J. Dent Res., 1998, vol. 77(8), pp. 1597-1605.

Samanta et al., "Crystal Structure of Human Plasma Platelet-activating Factor Acetylhydrolase," J. Biol. Chem., vol. 283(46), Nov. 14, 2008, pp. 31617-31624.

Sammes, "Naturally Occurring 2,5-Dioxopiperazines and Related Compounds," Fortschr. Chem. Org. Naturst., 1975, vol. 32, pp. 51-118.

Sano et al. "Process Research and Development of L-Alanyl-L-Glutamine, a Component of Parenteral Nutrition," Organic Process Research & Development, 2000, vol. 4, pp. 147-152.

Sato et al., "Comparison of the antiociceptive effect between the cyclic dipeptide cyclo[Tyr(Et)-homoarginine] and the linear dipeptide Boc-Tyr(Et)-homoarginine-Ome in rats.," Jpn J Pharmacol, Jan. 1984, vol. 34(1) (Abstract Only Provided).

Scharpe et al., "Peptide Truncation by Dipeptidyl Peptidase IV: A New Pathway for Drug Discovery," Verh K. Acad Geneeskd Belg. 2001, vol. 63(1), pp. 5-32 (Abstract Only Provided).

Schlingemann et al., "Role of vascular permeability factor/vascular endothelial growth factor in eye disease," Brit. J. Ophthalmology, vol. 81, 1997, pp. 501-512.

Sepetov et al., "Rearrangement, Racemization and Decomposition of Peptides in Aqueous Solution," Peptide Research, 1991, vol. 4(5), pp. 308-313 (Abstract Only Provided).

Seredenin et al. "Endogenous dipeptide cycloprolylglycine shows selective anxiolytic activity in animals with manifest fear reaction," Bull Exp Biol Med; Apr. 2002; vol. 1333(4) (Abstract Only Provided).

Shaw et al., "Future of early detection of lung cancer: the role of mouse models." Clin Cancer Res., Jul. 1; 11(13 Pt 2): 4999s-5003s, 2005.

Shimazaki et al., "Diketopiperazine Derivatives, a New Series of Platelet-Activating Factor Inhibitors," Chem. Pharm. Bull., 1987, vol. 35(8), pp. 3527-3530.

Shimazaki et al., "Diketopiperazines as a New Class of Platelet-Activating Factor Inhibitors," J. Med. Chem., 1987, vol. 30, pp. 1706-1709.

Shimazaki et al., "PAF Inhibitory Activity of Diketopiperazines: Structure-Activity Relationships," Lipids, 1991, vol. 26(12), pp. 1175-1178.

Shimi et al., "Isolation of Cairomycins A and C," Accession No. 1981:530895, retrieved from STN Oct. 6, 2010, p. 1.

Shimi et al., "Isolation of Cairomycins A and C," Antimicrobial Agents and Chemotherapy, Jun. 1981, vol. 19(6), pp. 941-944.

Shukla et al., "Role of Endogenous Cyclo(His-Pro) in Cold-Induced Hypothermia in the Desert Rat (*Mastomys natalensis*)," Peptides; 1994; 15(8):1471-4 (Abstract Only Provided).

Shutov et al., "[Diagnostic Significance of the type of In Vitro Interaction between Blood Lymphocytes and Serotonin in Multiple Sclerosis]," [Article in Russian], Zh Nevrol Psikhiatr Im S S Korsakova, 2002, vol. 102(4), pp. 35-38 (Abstract Only Provided).

Skates et al., "Molecular markers for early detection of renal carcinoma: investigative approach," Clin Cancer Res, Sep. 2004, vol. 10(18 Pt 2), pp. 6296S-6301S.

Smith et al., "Lesson 10, vol. 12—Asthma: Evolving Anti-Inflammatory Therapy," www.chestnet.org/education/pccu/vol12/ lesson10.html, pp. 1-8, printed Jul. 20, 2000.

Smith et al., "Recent developments in drug therapy for multiple sclerosis," Mult. Scler., 1999, vol. 5, pp. 110-120.

Smith et al., "Solid-phase synthesis of a library of piperazinediones and diazepinediones via Kaiser oxime resin." Bioorg. Med. Chem., 1998, vol. 8, pp. 2369-2374.

Sollid et al. "Is celiac disease an autoimmune disorder?" Current Opinion in Immunology, Dec. 2005, vol. 17, No. 6, pp. 595-600.

Sollis "Short and novel stereospecific synthesis of trisubstituted 2,5-diketopiperazines," J Org Chem, Jun. 2005, vol. 70(12), pp. 4735-4740 (Abstract Only Provided).

Song et al., "Synergistic Antidiabetic Activities of Zinc, Cyclo (His-Pro), and Arachidonic Acid," Metabolism 2001 50(1):53-59 (Abstract Only Provided).

Song et al., "Raw vegetable food containing high cyclo (his-pro) improved insulin sensitivity and body weight control," Metabolism, Nov. 2005, vol. 54(11), pp. 1480-1489 (Abstract Only Provided).

Stark et al., "Structures, sensory activity, and dose/response functions of 2,5-diketopiperazines in roasted cocoa nibs (*Theobroma cacao*)." J Agric Food Chem., Sep. 7, 2005, vol. 53(18), pp. 7222-7231 (Abstract Only Provided) PMID: 16131134.

Steiner et al., "Histidyl Proline Diketopiperazine (Cyclo [His-Pro]) in Eating Disorders," Neuropeptides, Oct. 1989, vol. 14(3), pp. 185-189 (Abstract Only Provided).

Strom et al., "*Lactobacillus plantarum* MiLAB 393 produces the antifungal cyclic dipeptides cyclo(L-Phe-L-Pro) and cyclo(L-Phe-trans-4-OH-L-Pro) and 3-phenyllactic acid.," Appl Environ Microbiol, Sep. 2002, vol. 68(9) (Abstract Only Provided).

Suzuki et al., "Effect of cyclic dipeptides containing histidine on pentobarbital narcosis," J. Pharm. Dyn., May 1981, vol. 4(5), pp. 377-379.

Takahara et al., "Detection in Human Serum by Radioimmunoassay of Histidyl-Proline Diketopiperazine, a Metabolite of Thyrotropin-Releasing Hormone," J Clinical Endocrinology, 1983, vol. 56(2), pp. 312-319 (Abstract Only Provided).

't Hart et al., "Evaluating the validity of animal models for research into therapies for immune-based disorders," DDT, 2004, vol. 9(12), pp. 517-524.

The Cytokine Handbook, edited by Thomson and Lotze, 4th edition, 2003 Academic Press, vol. I, London, UK, pp. 167-199, 456-474, 567-601.

The Cytokine Handbook, edited by Thomson and Lotze, 4th edition, 2003 Academic Press, vol. I, London, UK, pp. 169, 186, 187, 467, 570, 571, 838, 839, 1189-1193, 1197-1200.

The Cytokine Handbook, edited by Thomson and Lotze, 4th edition, 2003 Academic Press, vol. II, London, UK, pp. 838-860 and 1189-1211.

The Dictionary of Immunology, Fourth Edition, Edited by Herbert et al., 1995, pp. 51-52 and 69.

Unal et al., "Cyclo(Gly-Gln) inhibits the cardiorespiratory depression produced by beta-endorphin and morphine," Brain Research, 1997, vol. 747(1), pp. 52-59.

Vara et al., "PI3K/Akt signalling pathway and cancer," Cancer Treatment Reviews, 2004, vol. 30, pp. 193-204.

Varughese et al., "Crystal structure and conformation of cyclo-L-cystine," Int. J. Pept. Protein Res., vol. 18, Jul. 1981, pp. 88-102.

Vogel et al., "Disseminated tumor cells—Their detection and significance for prognosis of gastrointestinal and pancreatic carcinomas," Virchows Arch, 2001, vol. 439, pp. 109-117.

Walter et al., "Neurohypophyseal hormones, analogs, and fragments: their effect on puromycin-induced amnesia," Proc. Natl. Acad. Sci., Oct. 1975, vol. 72(10), pp. 4180-4184.

Walter et al., "The Cyclized C-Terminal Dipeptide of Arginine Vasopressin: Metabolic Stability and Antagonism of Puromycin-Induced Amnesia," Hormones and Behavior, 1982, vol. 16; p. 234-244.

Wang et al., "A facile pathway to synthesize diketopiperazine derivatives," Tetrahedron Lett, 2002, vol. 43, pp. 865-867.

Wang et al., "Novel inhibitors of plasminogen activator inhibitor-1: development of new templates from diketopiperazines," Bioorg Med Chem Lett, Sep. 2002, vol. 12(17), pp. 2367-2370 (Abstract Only Provided).

Weng et al., "Novel CCK-B receptor agonists: diketopiperazine analogues derived for CCK4 bioactive conformation," Regul Pept, Aug. 1996; vol. 65(1) (Abstract Only Provided).

Wennemers et al., "Diketopiperazine Receptors: A Novel Class of Highly Selective Receptors for Binding Small Peptides," Chem. Eur. J., 2001, vol. 7, No. 15, pp. 3342-3347.

Wilber et al., "Endogenous histidyl-proline diketopiperazine [cyclo (His-Pro)]: a potential satiety neuropeptide in normal and genetically obese rodents," Trans Assoc Am Physicians, 1983, vol. 96, pp. 131-136.

Wilber et al., "Histidyl-proline diketopiperazine: a potent and chronic appetite-inhibiting neuropeptide," Trans Assoc. Am Physicians, 1986, vol. 99, pp. 245-249.

Wilkes et al. "Patient Survival after Human Albumin Administration: A Meta-Analysis of Randomized, Controlled Trials." Annals of Internal Medicine, Aug. 2001, vol. 135, No. 3, pp. 149-164.

Wisniewski et al., "Relationship between serum cyclo (His-Pro) concentrations and the nutritional status of HIV-infected patients," South Med. J., Mar. 1994, vol. 87(3), pp. 348-351 (Abstract Only Provided).

Woehlecke et al., "Reversal of breast cancer resistance protein-mediated drug resistance by tryprostatin A.," Int J Cancer; Dec. 2003, vol. 107(5) (Abstract Only Provided).

Wolf et al., "Identification of Cyclo(His-Pro)-Like Immunoreactivity in Human Follicular Fluid: Correlation with Steroid and Peptide Hormones," J Soc Gynecol Investigation, 1994, vol. 1(3), pp. 220-224 (Abstract Only Provided).

Wretlind, "The Availability of the Isopropyl Ester of L- and D-Phenylalanine and 3,6-Dibenzyl-2,5-Diketopiperazine form Growth in Rats," Acta phys. Scandinav, May 1953, vol. 30, pp. 97-104.

Wyatt et al., "2,5-Diketopiperazines as potent and selective oxytocin antagonists 1: Identification, stereochemistry and initial SAR," Bioorg Med Chem Lett., May 16, 2005, vol. 15(10), pp. 2579-2582 (Abstract Only Provided) PMID: 15863320.

Yamada et al., "Abundance of Cyclo (His-Pro)-like Immunoreactivity in the Brain of TRH-Deficient Mice," Endocrinology, Jan. 1999, vol. 140(1), pp. 538-541 (Abstract Only Provided).

Yanagisawa et al., "The Subcellular and Organ Distribution and Natural Form of Histidyl-Proline Diketopiperazine in Rat Brain Determined by a Specific Radioimmunoassay," J Biol Chem, Nov. 10, 1980, vol. 255(21), pp. 10290-10294 (Abstract Only Provided).

Yang et al. "Increased hepatic platelet activating factor (PAF) and PAF receptors in carbon tetrachloride induced liver cirrhosis." Gut, Jan. 2004, vol. 53, No. 6, pp. 877-883.

Yi Es, "Hypersensitivity pneumonitis," Crit Rev Clin Lab Sci., Nov. 2002, vol. 39(6), pp. 581-629.

Yoshida et al., "PAF Inhibitors of Microbial Origin," Prog. Biochem. Pharmacol., 1988, vol. 22, pp. 68-80.

Youngblood et al., "Bovine Serum Albumin-GABA-His-Pro-NH2: an Immunogen for Production of Higher Affinity Antisera for TRH," J Neursci Methods, 1983, vol. 9(4), pp. 367-373 (Abstract Only Provided).

Zeng et al., "Synthesis of a small library of diketopiperazines as potential inhibitors of calpain," Bioorg Med Chem Lett, Jun. 2005, vol. 15(12), pp. 3034-3038.

Examiner's First Report for Australian Patent Application No. 2004241101, mailed Dec. 15, 2008, 2 pages.

Official Action for Australian Patent Application No. 2010203293, mailed Mar. 29, 2012 3 pages.

Official Action for Canadian Patent Application No. 2,523,467, dated Sep. 6, 2011, 3 pages.

Official Action for Canada Patent Application No. 2,523,467, dated Aug. 1, 2012 4 pages.

First Office Action (including translation) for Chinese Patent Application No. 2004800132490, issued Apr. 6, 2007, 10 pages.

Second Office Action (including translation) for Chinese Patent Application No. 2004800132490, issued Mar. 14, 2008, 4 pages.

Third Office Action (including translation) for Chinese Patent Application No. 2004800132490, issued Jun. 5, 2009, 11 pages.

English Translation of the Decision of Final Rejection of the Applications for Chinese Patent Application No. 2004800132490, issued Feb. 12, 2010, 10 pages.

Notification of Reexamination for Chinese Patent Application No. 200480013249.0, mailed Mar. 2, 2012 7 pages.

Decision of Reexamination for Chinese Patent Application No. 200480013249.0, dated Sep. 7, 2012, (English translation) 24 pages.

English Translation of First Office Action for Chinese Patent Application No. 200810081995.3, issuing date Mar. 8, 2010, 4 pages.

English Translation of Final Rejection for Chinese Patent Application No. 200810081995.3, issued Feb. 24, 2011, 3 pages.

English Translation of First Office Action for Chinese Patent Application No. 201010193231.0, issued Jul. 21, 2011, 2 pages.

Official Action for Chinese Patent Application No. 201010193231.0, dated Aug. 28, 2012, (English translation of Examiner's Comments only) 2 pages.

Official Action for China Patent Application No. 201110147118.3, dated Jan. 5, 2012, (English translation of Examiner's Comments only) 5 pages.

Supplementary European Search Report for European Patent Application No. 04752368.3, dated Jan. 15, 2010, 6 pages.

Official Action for European Patent Application No. 04752368.3, dated Jul. 20, 2010, 10 pages.

Extended European Search Report for European Patent Application No. 12005458.0, dated Sep. 28, 2012 6 pages.

Partial European Search Report for European Patent Application No. 12005455.6, dated Nov. 8, 2012, 5 pages.

Official Action for Israel Patent Application No. 171961, dated Oct. 31, 2010, 5 pages (including translation).

Official Action for Israel Patent Application No. 171961, dated Aug. 30, 2011, 3 pages (including translation).

First Examination Report for Indian Patent Application No. 5484/DELNP/2005, mailed May 21, 2008, 12 pages.

Official Action for Japanese Patent Application No. 2006-533125, mailed Oct. 5, 2010, 7 pages (translation only).

Official Action for Japanese Patent Application No. 2006-533125, mailed Feb. 8, 2011, 10 pages (English translation only).

Official Action for Japanese Patent Application No. 2006-533125, mailed Oct. 4, 2011, (English translation only), 6 pages.

Official Action for Japanese Patent Application No. 2010-292763, mailed Oct. 30, 2012, (with English translation) 6 pages.

Official Action for Korean Patent Application No. 10-2005-7021755, mailed Feb. 18, 2011, (including English translation) 15 pages.

Official Action for Korea Patent Application No. 10-2012-7014047, dated Aug. 29, 2012, (with English Summary) 7 pages.

Examination Report for New Zealand Patent Application No. 542886, mailed Nov. 28, 2007, 3 pages.

Examination Report for New Zealand Patent Application No. 576931, mailed May 18, 2009, 2 pages.

Examination Report for New Zealand Patent Application No. 576931, dated Sep. 28, 2010, 2 pages.

Examination Report for New Zealand Patent Application No. 586516, dated Jul. 1, 2010, 2 pages.
Examination Report for New Zealand Patent Application No. 586516, dated Aug. 4, 2011, 2 pages.
Written Opinion for Singapore Patent Application No. 200506561-0, dated Jan. 18, 2007, 5 pages.
Examination Report for Singapore Patent Application No. 200506561-0, dated Sep. 14, 2007, 4 pages.
Written Opinion for International (PCT) Patent Application No. PCT/US2004/015340, mailed May 12, 2005, 5 pages.
International Search Report for International (PCT) Patent Application No. PCT/US2004/015340, mailed May 12, 2005, 1 page.
International Preliminary Report on Patentability for International (PCT) Patent Application No. PCT/US2004/015340, mailed Dec. 1, 2005, 6 pages.
"Centricon Centrifugal Filter Devices User Guide," Millipore Corp., Mar. 2005, 23 pages.
Albert et al., "ABT-491, a highly potent and selective PAF antagonist, inhibits nasal vascular permeability associated with experimental allergic rhinitis in Brown Norway rats," Inflamm. Res., 1997, Supplement 2, pp. S133-S134.
Berman et al., "Psoriasis," PubMed Health, reviewed Nov. 22, 2011, available at www.ncbi.nlm.nih.gov/pubmedhealth/PMH0001470/?report=printable.
Lee et al., "Characterization of an Elastase Inhibitor Produced by *Streptomyces lavendulae* SMF11," Journal of Microbiology and Biotechnology, 2000, vol. 10, No. 1, pp. 81-85
Nakamura et al., "T-cell mediated inflammatory pathway in osteoarthritis," Osteoarthritis & Cartilage, 1999, vol. 7, pp. 401-402.
Neustadt, "Intra-articular injections for osteoarthritis of the knee," Cleveland Clinic J. Med., 2006, vol. 73(10), pp. 897-911.
O'Connor et al., "Post-proline dipeptidyl-aminopeptidase from synaptosomal membranes of guinea-pig brain," European Journal of Biochemistry, 1986, vol. 154, Iss. 2, pp. 329-335.
Teitel et al., "Rheumatoid arthritis," PubMed Health, reviewed Feb. 2, 2012, available at www.ncbi.nlm.nih.gov/pubmedhealth/PMH0001467/?report=printable, 8 pages.
Teitel et al., "Scleroderma," PubMed Health, reviewed Feb. 2, 2012, available at www.ncbi.nlm.nih.gov/pubmedhealth/PMH0001465/?report=printable, 7 pages.
Teitel et al., "Systemic lupus erythematosus," PubMed Health, reviewed Feb. 2, 2012, available at www.ncbi.nlm.nih.gov/pubmedhealth/PMH0001471/?report=printable, 9 pages.
Zieve, "Multiple sclerosis," PubMed Health, reviewed Sep. 26, 2011, available at www.ncbi.nlm.nih.gov/pubmedhealth/PMH0001747/?report=printable, 10 pages.
Extended European Search Report for European Patent Application No. 12005455.6, dated Mar. 6, 2013, 10 pages.
Extended European Search Report for European Patent Application No. 12005456.4 dated Feb. 21, 2013, 12 pages.
Extended European Search Report for European Patent Application No. 12005457.2, dated Mar. 21, 2013, 10 pages.
Extended European Search Report for European Patent Application No. 12005454.9, dated Mar. 12, 2013, 10 pages.
Bar-Or et al. "Commercial human albumin preparations for clinical use are immunosuppressive in vitro," Critical Care Medicine, Jun. 2006, vol. 34, No. 6, pp. 1707-1712 (Abstract Only) (downloaded from : journals.lww.com).
English Translation of Decision of Reexamination for China Patent Application No. 200810081995.3, dated Nov. 9, 2012 11 pages.
English Translation of Official Action for China Patent Application No. 201110147118.3, dated Oct. 30, 2012 6 pages.
Partial Search Report for European Patent Application No. 12005456.4, dated Nov. 12, 2012 6 pages.
Partial Search Report for European Patent Application No. 12005457.2, dated Dec. 21, 2012 6 pages.
Partial Search Report for European Patent Application No. 12005454.9, dated Nov. 12, 2012 6 pages.
Official Action (with English Summary) for Korean Patent Application No. 10-2012-7014047, mailed May 2, 2013, 4 pages.
Gomez et al., "Low-Dose Dopamine Agonist Administration Blocks Vascular Endothelial Growth Factor (VEGF)-Mediated Vascular Hyperpermeability without Altering VEGF Receptor 2-Dependent Luteal Angiogenesis in a Rat Ovarian Hyperstimulation Model," Endocrinology, 2006, vol. 147, No. 11, pp. 5400-5411.
US 8,129,392, 03/2012, Bar-Or (withdrawn)

* cited by examiner

TREATMENT OF T-CELL MEDIATED DISEASES

This application is a continuation of U.S. application Ser. No. 12/753,671, filed Apr. 2, 2010, which is a continuation of U.S. application Ser. No. 10/846,482, filed May 14, 2004, now U.S. Pat. No. 7,732,403 which claims benefit of provisional application Nos. 60/471,017, filed May 15, 2003; 60/489,270, filed Jul. 21, 2003; 60/514,930, filed Oct. 27, 2003; and 60/517,338, filed Nov. 4, 2003, the complete disclosures of which are incorporated herein by reference.

FIELD OF THE INVENTION

This invention relates to the treatment of T-cell mediated diseases and to the inhibition of the activation of T-cells using certain diketopiperazines. The invention also relates to pharmaceutical compositions comprising certain diketopiperazines and to methods of synthesizing diketopiperazines. The invention further relates to methods of making improved pharmaceutical compositions of proteins and peptides to either increase or decrease the content of diketopiperazines in the compositions and to the resultant improved pharmaceutical compositions.

BACKGROUND

T-cell mediated diseases represent a large number of immune system disorders. In particular, T-cells are thought to be the cells that start and perpetuate autoimmune diseases. Autoimmune diseases are a group of eighty serious, chronic illnesses that afflict millions of people in the United States alone. Autoimmune diseases are characterized by reactivity of the immune system to endogenous (self) antigens. These immune responses to self antigens are maintained by the persistent or recurrent activation of self-reactive T-cells and, directly or indirectly, the self-reactive T-cells are responsible for the characteristic tissue injury and destruction seen in autoimmune diseases. Although many treatments for autoimmune diseases and other T-cell mediated diseases have been proposed, there is still a need for additional treatments.

SUMMARY OF THE INVENTION

The present invention provides a method of treating T-cell mediated diseases. The method comprises administering to an animal in need thereof an effective amount of a diketopiperazine having the following formula:

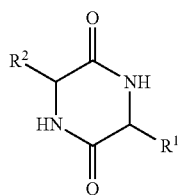

(I)

wherein:
$R^1$ and $R^2$, which may be the same or different, each is:
(a) a side chain of an amino acid, wherein the amino acid is glycine, alanine, valine, norvaline, α-aminoisobutyric acid, 2,4-diaminobutyric acid, 2,3-diaminobutyric acid, leucine, isoleucine, norleucine, serine, homoserine, threonine, aspartic acid, asparagine, glutamic acid, glutamine, lysine, hydroxylysine, histidine, arginine, homoarginine, citrulline, phenylalanine, p-aminophenylalanine, tyrosine, tryptophan, thyroxine, cysteine, homocysteine, methionine, penicillamine or ornithine; provided, however, that when $R^1$ is the side chain of asparagine or glutamine, then $R^2$ cannot be the side chain of lysine or ornithine, and when $R^1$ is the side chain of lysine or ornithine, then $R^2$ cannot be the side chain of asparagine or glutamine;
(b) $R^1$ is —$CH_2$—$CH_2$—$CH_2$— or —$CH_2$—$CH(OH)$—$CH_2$— and together with the adjacent ring nitrogen forms proline or hydroxyproline and/or $R^2$ is —$CH_2$—$CH_2$—$CH_2$— or —$CH_2$—$CH(OH)$—$CH_2$— and together with the adjacent ring nitrogen forms proline or hydroxyproline; or
(c) a derivative of a side chain of an amino acid, wherein the amino acid is one of those recited in (a), and the derivatized side chain has:
(i) an —$NH_2$ group replaced by an —$NHR^3$ or —$N(R^3)_2$ group, wherein each $R^3$ may independently be a substituted or unsubstituted alkyl, cycloalkyl, heterocycloalkyl, aryl, alkylaryl, arylalkyl or heteroaryl;
(ii) an —OH group replaced by an —O—$PO_3H_2$ or —$OR^3$ group, wherein each $R^3$ may independently be a substituted or unsubstituted alkyl, cycloalkyl, heterocycloalkyl, aryl, alkylaryl, arylalkyl or heteroaryl;
(iii) a —COOH group replaced by a —$COOR^3$ group, wherein each $R^3$ may independently be a substituted or unsubstituted alkyl, cycloalkyl, heterocycloalkyl, aryl, alkylaryl, arylalkyl or heteroaryl;
(iv) a —COOH group replaced by a —$CON(R^4)_2$ group, wherein each $R^4$ may independently be H or a substituted or unsubstituted alkyl, cycloalkyl, heterocycloalkyl, aryl, alkylaryl, arylalkyl or heteroaryl;
(v) an —SH group replaced by —S—S—$CH_2$—CH($NH_2$)—COOH or —S—S—$CH_2$—$CH_2$—CH($NH_2$)—COOH;
(vi) a —$CH_2$— group replaced by a —$CH(NH_2)$— or a —$CH(OH)$— group;
(vii) a —$CH_3$ group replaced by a —$CH_2$—$NH_2$ or a —$CH_2$—OH group; and/or
(viii) an H which is attached to a carbon atom replaced by a halogen; or
a physiologically-acceptable salt thereof.

The invention also provides a method of inhibiting the activation of T-cells. The method comprises administering to an animal in need thereof an effective amount of a diketopiperazine of formula I or a physiologically-acceptable salt thereof.

The invention further provides a pharmaceutical composition comprising a pharmaceutically-acceptable carrier and a diketopiperazine having the following formula:

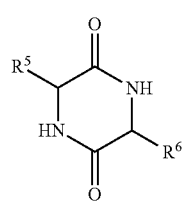

(II)

wherein:
$R^5$ and $R^6$, which may be the same or different, each is:

(a) a side chain of an amino acid, wherein the amino acid is glycine, alanine, valine, norvaline, α-aminoisobutyric acid, 2,4-diaminobutyric acid, 2,3-diaminobutyric acid, leucine, isoleucine, norleucine, serine, homoserine, threonine, lysine, hydroxylysine, histidine, arginine, homoarginine, citrulline, phenylalanine, p-aminophenylalanine, tyrosine, tryptophan, thyroxine or ornithine; provided, however, that when $R^5$ is the side chain of asparagine or glutamine, then $R^6$ cannot be the side chain of lysine or ornithine, and when $R^5$ is the side chain of lysine or ornithine, then $R^6$ cannot be the side chain of asparagine or glutamine;

(b) $R^5$ is —$CH_2$—$CH_2$—$CH_2$— or —$CH_2$—$CH(OH)$—$CH_2$— and together with the adjacent ring nitrogen forms proline or hydroxyproline and/or $R^6$ is —$CH_2$—$CH_2$—$CH_2$— or —$CH_2$—$CH(OH)$—$CH_2$— and together with the adjacent ring nitrogen forms proline or hydroxyproline; or (c) a derivative of a side chain of an amino acid, wherein the amino acid is one of those recited in (a), and the derivatized side chain has:

(i) an —$NH_2$ group replaced by an —$NHR^3$ or —$N(R^3)_2$ group, wherein each $R^3$ may independently be a substituted or unsubstituted alkyl, cycloalkyl, heterocycloalkyl, aryl, alkylaryl, arylalkyl or heteroaryl;

(ii) an —OH group replaced by an —O—$PO_3H_2$ or —$OR^3$ group, wherein each $R^3$ may independently be a substituted or unsubstituted alkyl, cycloalkyl, heterocycloalkyl, aryl, alkylaryl, arylalkyl or heteroaryl;

(iii) a —$CH_2$— group replaced by a —$CH(NH_2)$— or a —$CH(OH)$— group;

(iv) a —$CH_3$ group replaced by a —$CH_2$—$NH_2$ or a —$CH_2$—OH group; and/or (v) an H which is attached to a carbon atom replaced by a halogen; or a physiologically-acceptable salt thereof.

The invention provides another method of treating a T-cell mediated disease. The method comprises administering to an animal in need thereof an effective amount of a pharmaceutical composition comprising a protein or peptide normally found in the animal, the protein or peptide having been treated so that the composition also comprises at least one diketopiperazine derived from the protein or peptide.

The invention further provides a method of inhibiting T-cell activation. The method comprises administering to an animal in need thereof an effective amount of a pharmaceutical composition comprising a protein or peptide normally found in the animal, the protein or peptide having been treated so that the composition also comprises at least one diketopiperazine derived from the protein or peptide.

In addition, the invention provides methods of synthesizing diketopiperazines. In one embodiment, the method comprises heating a solution of a protein or peptide under conditions effective to cause the formation of a diketopiperazine. In a second embodiment, the method comprises contacting a solution of a protein or peptide with an enzyme that cleaves the two N-terminal or the two C-terminal amino acids of the protein or peptide under conditions effective to produce a diketopiperazine.

The invention also provides an improved pharmaceutical composition of a protein or peptide. The improvement is that the composition comprises a decreased content of diketopiperazines.

In addition, the invention provides a method of making an improved pharmaceutical composition of a protein or peptide. The method comprises removing from the composition at least some of the diketopiperazines present in the composition.

The invention further provides a method of making an improved pharmaceutical composition of a protein or peptide. The method comprises treating a solution of the protein or peptide so as to increase the content of diketopiperazines in the composition.

The invention also provides an improved pharmaceutical composition of a protein or peptide. The improvement is that the composition comprises an increased content of diketopiperazines.

DETAILED DESCRIPTION OF THE PRESENTLY-PREFERRED EMBODIMENTS

Figure 1:
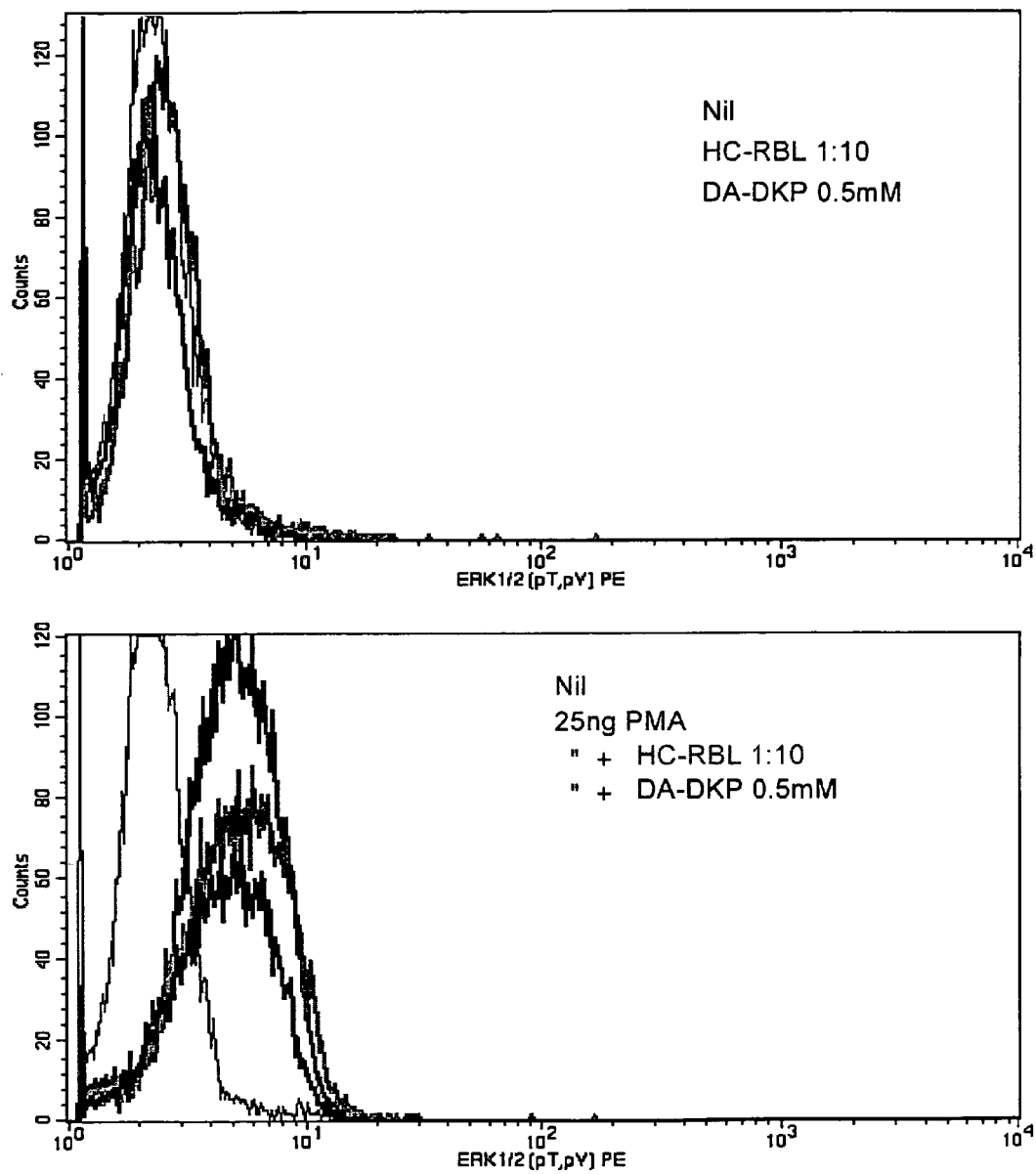
FIG. 1. Tracings of counts versus concentration of ERK1/2 for TriPS cells (CD4+ T-cell line isolated from influenza-immunized donor which is specific for hemagglutinin) isolated on day 20 after stimulation with anti-CD3 OKT3 antibody and incubated with 25 ng phorbal myristic acid (PMA), HC-RBL (fraction of heated human colostrum of molecular weight less than 3 kD and containing MR-DKP) at a 1:10 dilution and 0.5 mM DA-DKP for 15 minutes at 37° C.

The present invention provides a method of treating T-cell mediated diseases. "Treat" is used herein to mean to reduce (wholly or partially) the symptoms, duration or severity of a disease, including curing the disease, or to prevent the disease.

T-cell mediated diseases include graft rejection, graft versus host disease, unwanted delayed-type hypersensitivity reactions (such as delayed-type allergic reactions), T-cell mediated pulmonary diseases, and autoimmune diseases. T-cell mediated pulmonary diseases include sarcoidosis, hypersensitivity pneumonitis, acute interstitial pneumonitis, alveolitis, pulmonary fibrosis, idiopathic pulmonary fibrosis and other diseases characterized by inflammatory lung damage. Autoimmune diseases include multiple sclerosis, neuritis, polymyositis, psoriasis, vitiligo, Sjogren's syndrome, rheumatoid arthritis, Type 1 diabetes, autoimmune pancreatitis, inflammatory bowel diseases (e.g., Crohn's disease and ulcerative colitis), celiac disease, glomerulonephritis, scleroderma, sarcoidosis, autoimmune thyroid diseases (e.g., Hashimoto's thyroiditis and Graves disease), myasthenia gravis, Addison's disease, autoimmune uveoretinitis, pemphigus vulgaris, primary biliary cirrhosis, pernicious anemia, and systemic lupus erythematosis.

The T-cell mediated disease are treated by administering to an animal in need thereof an effective amount of a diketopiperazine having the following formula:

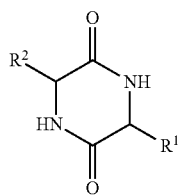

(I)

wherein:
$R^1$ and $R^2$, which may be the same or different, each is:
(a) a side chain of an amino acid, wherein the amino acid is glycine, alanine, valine, norvaline, α-aminoisobutyric acid, 2,4-diaminobutyric acid, 2,3-diaminobutyric acid, leucine, isoleucine, norleucine, serine, homoserine, threonine, aspartic acid, asparagine, glutamic acid, glutamine, lysine, hydroxylysine, histidine, arginine, homoarginine, citrulline, phenylalanine, p-aminophenylalanine, tyrosine, tryptophan, thyroxine, cysteine, homocysteine, methionine, penicillamine or ornithine; provided, however, that when $R^1$ is the side chain of asparagine or glutamine, then $R^2$ cannot be the side chain of lysine or ornithine, and when $R^1$ is the side chain of lysine or ornithine, then $R^2$ cannot be the side chain of asparagine or glutamine;
(b) $R^1$ is —$CH_2$—$CH_2$—$CH_2$— or —$CH_2$—$CH(OH)$—$CH_2$— and together with the adjacent ring nitrogen forms proline or hydroxyproline and/or $R^2$ is —$CH_2$—$CH_2$—$CH_2$— or —$CH_2$—$CH(OH)$—$CH_2$— and together with the adjacent ring nitrogen forms proline or hydroxyproline; or
(c) a derivative of a side chain of an amino acid, wherein the amino acid is one of those recited in (a), and the derivatized side chain has:
  (i) an —$NH_2$ group replaced by an —$NHR^3$ or —$N(R^3)_2$ group, wherein each $R^3$ may independently be a substituted or unsubstituted alkyl, cycloalkyl, heterocycloalkyl, aryl, alkylaryl, arylalkyl or heteroaryl;
  (ii) an —OH group replaced by an —O—$PO_3H_2$ or —$OR^3$ group, wherein each $R^3$ may independently be a substituted or unsubstituted alkyl, cycloalkyl, heterocycloalkyl, aryl, alkylaryl, arylalkyl or heteroaryl;
  (iii) a —COOH group replaced by a —$COOR^3$ group, wherein each $R^3$ may independently be a substituted or unsubstituted alkyl, cycloalkyl, heterocycloalkyl, aryl, alkylaryl, arylalkyl or heteroaryl;
  (iv) a —COOH group replaced by a —$CON(R^4)_2$ group, wherein each $R^4$ may independently be H or a substituted or unsubstituted alkyl, cycloalkyl, heterocycloalkyl, aryl, alkylaryl, arylalkyl or heteroaryl;
  (v) an —SH group replaced by —S—S—$CH_2$—CH($NH_2$)—COOH or —S—S—$CH_2$—$CH_2$—CH($NH_2$)—COOH;
  (vi) a —$CH_2$— group replaced by a —CH($NH_2$)— or a —CH(OH)— group;
  (vii) a —$CH_3$ group replaced by a —$CH_2$—$NH_2$ or a —$CH_2$—OH group; and/or
  (viii) an H which is attached to a carbon atom replaced by a halogen; or
a physiologically-acceptable salt thereof.

By "replaced" is meant that, with reference to the formula of an amino acid side chain, the specified group is replaced by the other specified group. For instance, the formula of the isoleucine side chain is —CH($CH_3$)—$CH_2$—$CH_3$. If the terminal —$CH_3$ group is replaced with a —$CH_2$—OH group, then the formula of the resulting derivatized isoleucine side chain would be —CH($CH_3$)—$CH_2$—$CH_2$—OH. As another example, the formula of the alanine side chain is —$CH_3$. If one of the hydrogen atoms is replaced by a chlorine atom, then the resulting derivatized alanine side chain would be —$CH_2$—Cl. Note that the side chain of glycine is —H and, if this H is replaced by a chlorine (or other halogen) atom, the resulting side chain will —Cl, with the chlorine atom attached to the ring carbon (e.g., $R^1$=—Cl)

Preferred are diketopiperazines wherein $R^1$, $R^2$ or both is the side chain of aspartic acid or glutamic acid or a derivative of such a side chain wherein the —COOH group is replaced by a —$COOR^3$ group or a —$CON(R^4)_2$ group, wherein $R^3$ and $R^4$ are defined above. Of this group of compounds, most preferred are diketopiperazines comprising the side chains of aspartic acid and alanine (Asp-Ala DKP or DA-DKP), the side chains of glutamic acid and alanine (Glu-Ala DKP or EA-DKP), the side chains of tyrosine and aspartic acid (Tyr-Asp DKP or YD-DKP), the side chains of tyrosine and glutamic acid (Tyr-Glu DKP or YE-DKP) and derivatives of the aspartic acid or glutamic acid side chains of these four diketopiperazines wherein the —COOH group is replaced by a —$COOR^3$ group or a —$CON(R^4)_2$ group, wherein $R^3$ and $R^4$ are defined above.

Also, preferred are diketopiperazines wherein $R^1$ and $R^2$ are both hydrophobic side chains (e.g., the side chain of phenylalanine) or hydrophobic side chain derivatives. By "hydrophobic side chain derivative" is meant that the derivatized side chain which is hydrophobic. In particular, preferred are diketopiperzines wherein $R^1$ and/or $R^2$, which may be the same or different, each is the side chain of glycine, alanine, valine, norvaline, α-aminobutyric acid, leucine, isoleucine, norleucine or phenylalanine, and/or $R^1$ and/or $R^2$ is —$CH_2$—$CH_2$—$CH_2$— and together with the adjacent nitrogen atom(s) form proline. Of this group of compounds, most preferred are the diketopiperazines comprising the side chains of glycine and leucine (Gly-Leu DKP or GL-DKP), proline and phenylalanine (Pro-Phe DKP or PF-DKP), and alanine and proline (Ala-Pro DKP or AP-DKP)

Additional preferred diketopiperazines are those wherein $R^1$, $R^2$ or both is the side chain of methionine, the side chain of arginine or a derivative of these side chains. Most preferred of this group is a diketopiperazine wherein $R^1$ is the side chain of methionine and $R^2$ is the side chain of arginine (Met-Arg DKP or MR-DKP).

By "side chain" of an amino acid is meant that portion of the amino acid attached to the common $NH_2$—CH—COOH backbone of all of the amino acids listed above. For instance, the side chain of glycine is —H, the side chain of alanine is —$CH_3$, and the side chain of serine is —$CH_2OH$.

By "hydrophobic" is meant a side chain or side chain derivative that is uncharged at physiological pH and is repelled by an aqueous solution.

By "alkyl" is meant a saturated straight-chain or branched hydrocarbon containing 1-10 carbon atoms, preferably 1-6, carbon atoms. "Lower alkyl" means a saturated straight-chain or branched hydrocarbon containing 1-6 carbon atoms.

By "cycloalkyl" is meant a saturated cyclic hydrocarbon containing at least one ring, each ring containing at least three carbon atoms. Preferably, the cycloalkyl contains one ring of 4-8 carbon atoms.

By "heterocycloalkyl" is meant a cycloalkyl having one or more of the ring carbon atoms of at least one of the rings replaced by an O, S or N.

By "aryl" is meant an aromatic group having at least one aromatic ring (e.g., phenyl).

By "alkylaryl" is meant a lower alkyl having an H replaced by an aryl (e.g., —$CH_2$—$C_6H_5$ or —$CH_3CH(C_6H_5)CH_3$).

By "arylalkyl" is meant an aryl having an H replaced by a lower alkyl (e.g., —$C_6H_4$—$CH_3$).

By "heteroaryl" is meant an aryl having one or more of the ring carbon atoms of at least one of the rings replaced by an O, S or N.

By "substituted" is meant that the moiety is substituted with one or more substituents selected from the following group: —OH, $NH_2$, —SH, —COOH and/or a halogen atom.

By "halogen" is meant chlorine, fluorine, bromine or iodine. Preferred is chlorine or bromine.

The diketopiperazines of formula I are effective in treating T-cell mediated diseases because they inhibit the activation of T-cells. Accordingly, the diketopiperazines of formula I can also be used to treat inflammation and inflammatory diseases which are caused by, exacerbated by, or involve activated T-cells. "Inhibit" is used herein to mean to reduce (wholly or partially) or to prevent.

Methods of making diketopiperazines are well known in the art, and these methods may be employed to synthesize the diketopiperazines of the invention. See, e.g., U.S. Pat. Nos. 4,694,081, 5,817,751, 5,990,112, 5,932,579 and 6,555,543, US Patent Application Publication Number 2004/0024180, PCT applications WO 96/00391 and WO 97/48685, and Smith et al., *Bioorg. Med. Chem. Letters*, 8, 2369-2374 (1998), the complete disclosures of which are incorporated herein by reference.

For instance, diketopiperazines can be prepared by first synthesizing dipeptides. The dipeptides can be synthesized by methods well known in the art using L-amino acids, D-amino acids or a combination of D- and L-amino acids. Preferred are solid-phase peptide synthetic methods. Of course, dipeptides are also available commercially from numerous sources, including DMI Synthesis Ltd., Cardiff, UK (custom synthesis), Sigma-Aldrich, St. Louis, Mo. (primarily custom synthesis), Phoenix Pharmaceuticals, Inc., Belmont, Calif. (custom synthesis), Fisher Scientific (custom synthesis) and Advanced ChemTech, Louisville, Ky.

Once the dipeptide is synthesized or purchased, it is cyclized to form a diketopiperazine. This can be accomplished by a variety of techniques. For example, U.S. Patent Application Publication Number 2004/0024180 describes a method of cyclizing dipeptides. Briefly, the dipeptide is heated in an organic solvent while removing water by distillation. Preferably, the organic solvent is a low-boiling azeotrope with water, such as acetonitrile, allyl alcohol, benzene, benzyl alcohol, n-butanol, 2-butanol, t-butanol, acetic acid butylester, carbon tetrachloride, chlorobenzene chloroform, cyclohexane, 1,2-dichlorethane, diethylacetal, dimethylacetal, acetic acid ethylester, heptane, methylisobutylketone, 3-pentanol, toluene and xylene. The temperature depends on the reaction speed at which the cyclization takes place and on the type of azeotroping agent used. The reaction is preferably carried out at 50-200° C., more preferably 80-150° C. The pH range in which cyclization takes place can be easily determine by the person skilled in the art. It will advantageously be 2-9, preferably 3-7.

When one or both of the amino acids of the dipeptide has, or is derivatized to have, a carboxyl group on its side chain (e.g., aspartic acid or glutamic acid), the dipeptide is preferably cyclized as described in U.S. Pat. No. 6,555,543. Briefly, the dipeptide, with the side-chain carboxyl still protected, is heated under neutral conditions. Typically, the dipeptide will be heated at from about 80° C. to about 180° C., preferably at about 120° C. The solvent will be a neutral solvent. For instance, the solvent may comprise an alcohol (such as butanol, methanol, ethanol, and higher alcohols, but not phenol) and an azeotropic co-solvent (such as toluene, benzene, or xylene). Preferably, the alcohol is butan-2-ol, and the azeotropic co-solvent is toluene. The heating is continued until the reaction is complete, and such times can be determined empirically. Typically, the dipeptide will be cyclized by refluxing it for about 8-24 hours, preferably about 18 hours. Finally, the protecting group is removed from the diketopiperazine. In doing so, the use of strong acids (mineral acids, such as sulfuric or hydrochloric acids), strong bases (alkaline bases, such as potassium hydroxide or sodium hydroxide), and strong reducing agents (e.g., lithium aluminum hydride) should be avoided, in order to maintain the chirality of the final compound.

Dipeptides made on solid phase resins can be cyclized and released from the resin in one step. See, e.g., U.S. Pat. No. 5,817,751. For instance, the resin having an N-alkylated dipeptide attached is suspended in toluene or toluene/ethanol in the presence of acetic acid (e.g., 1%) or triethylamine (e.g., 4%). Typically, basic cyclization conditions are preferred for their faster cyclization times.

To prepare the diketopiperazine of formulas I and II wherein the amino acid side chains are derivatized, amino acid derivatives can be used in the synthesis of the dipeptides, the dipeptides can be derivatized and/or the diketopiperazines can be derivatized, as is known in the art. See, e.g., those references cited above.

Other methods of cyclizing dipeptides and of making diketopiperazines are known in the art and can be used in the preparation of diketopiperazines useful in the practice of the invention. See, e.g., those references listed above. In addition, many diketopiperazines suitable for use in the present invention can be made as described below from proteins and peptides. Further, diketopiperazines for use in the practice of the invention can be obtained commercially from, e.g., DMI Synthesis Ltd., Cardiff, UK (custom synthesis).

The diketopiperazines of formulas I and II include all possible stereoisomers than can be obtained by varying the configuration of the individual chiral centers, axes or surfaces. In other words, the diketopiperazines of formulas I and II include all possible diastereomers, as well as all optical isomers (enantiomers).

The physiologically-acceptable salts of the diketopiperazines of the invention may also be used in the practice of the invention. Physiologically-acceptable salts include conventional non-toxic salts, such as salts derived from inorganic acids (such as hydrochloric, hydrobromic, sulfuric, phosphoric, nitric, and the like), organic acids (such as acetic, propionic, succinic, glycolic, stearic, lactic, malic, tartaric, citric, glutamic, aspartic, benzoic, salicylic, oxalic, ascorbic acid, and the like) or bases (such as the hydroxide, carbonate or bicarbonate of a pharmaceutically-acceptable metal cation or organic cations derived from N,N-dibenzylethylenediamine, D-glucosamine, or ethylenediamine). The salts are prepared in a conventional manner, e.g., by neutralizing the free base form of the compound with an acid.

As noted above, a diketopiperazine of the invention, or a physiologically-acceptable salt thereof, can be used to treat a T-cell mediated disease or to inhibit activation of T-cells. To do so, a diketopiperazine, or a physiologically-acceptable salt thereof, is administered to an animal in need of treatment. Preferably, the animal is a mammal, such as a rabbit, goat, dog, cat, horse or human. Effective dosage forms, modes of administration and dosage amounts for the compounds of the invention may be determined empirically, and making such determinations is within the skill of the art. It is understood by those skilled in the art that the dosage amount will vary with the particular compound employed, the disease or condition to be treated, the severity of the disease or condition, the route(s) of administration, the rate of excretion of the compound, the duration of the treatment, the identify of any other drugs being administered to the animal, the age, size and species of the animal, and like factors known in the medical and veterinary arts. In general, a suitable daily dose of a compound of the present invention will be that amount of the compound which is the lowest dose effective to produce a therapeutic effect. However, the daily dosage will be determined by an attending physician or veterinarian within the scope of sound medical judgment. If desired, the effective daily dose may be administered as two, three, four, five, six or more sub-doses, administered separately at appropriate intervals throughout the day. Administration of the compound should be continued until an acceptable response is achieved.

The compounds of the present invention (i.e., diketopiperazines and physiologically-acceptable salts thereof) may be administered to an animal patient for therapy by any suitable route of administration, including orally, nasally, rectally, vaginally, parenterally (e.g., intravenously, intraspinally, intraperitoneally, subcutaneously, or intramuscularly), intracisternally, transdermally, intracranially, intracerebrally, and topically (including buccally and sublingually). The preferred routes of administration are orally and intravenously.

While it is possible for a compound of the present invention to be administered alone, it is preferable to administer the compound as a pharmaceutical formulation (composition). The pharmaceutical compositions of the invention comprise a compound or compounds of the invention as an active ingredient in admixture with one or more pharmaceutically-acceptable carriers and, optionally, with one or more other compounds, drugs or other materials. Each carrier must be "acceptable" in the sense of being compatible with the other ingredients of the formulation and not injurious to the animal. Pharmaceutically-acceptable carriers are well known in the art. Regardless of the route of administration selected, the compounds of the present invention are formulated into pharmaceutically-acceptable dosage forms by conventional methods known to those of skill in the art. See, e.g., *Remington's Pharmaceutical Sciences*.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds of the present invention as an active ingredient. A compound or compounds of the present invention may also be administered as bolus, electuary or paste.

In solid dosage forms of the invention for oral administration (capsules, tablets, pills, dragees, powders, granules and the like), the active ingredient (i.e., one or more diketopiperazines of the invention and/or physiologically-acceptable salts thereof) is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active ingredient, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or salicylate, and which is solid at room temperature, but liquid at body temperature and, therefore, will melt in the rectum or vaginal cavity and release the active compound. Formulations of the present invention which are suitable for vaginal administration also include pessaries, tampons, creams, gels, pastes, foams or spray formulations containing such carriers as are known in the art to be appropriate.

Dosage forms for the topical or transdermal administration of compounds of the invention include powders, sprays, ointments, pastes, creams, lotions, gels, solutions, patches, drops and inhalants. The active ingredient may be mixed under sterile conditions with a pharmaceutically-acceptable carrier, and with any buffers, or propellants which may be required.

The ointments, pastes, creams and gels may contain, in addition to the active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the active ingredient, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of compounds of the invention to the body. Such dosage forms can be made by dissolving, dispersing or otherwise incorporating one or more compounds of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Pharmaceutical formulations include those suitable for administration by inhalation or insufflation or for nasal or intraocular administration. For administration to the upper (nasal) or lower respiratory tract by inhalation, the compounds of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of one or more compounds of the invention and a suitable powder base, such as lactose or starch. The powder composition may be presented in unit dosage form in, for example, capsules or cartridges, or, e.g., gelatin or blister packs from which the powder may be administered with the aid of an inhalator, insufflator or a metered-dose inhaler.

For intranasal administration, compounds of the invention may be administered by means of nose drops or a liquid spray, such as by means of a plastic bottle atomizer or metered-dose inhaler. Typical of atomizers are the Mistometer (Wintrop) and Medihaler (Riker).

Drops, such as eye drops or nose drops, may be formulated with an aqueous or nonaqueous base also comprising one or more dispersing agents, solubilizing agents or suspending agents. Liquid sprays are conveniently delivered from pressurized packs. Drops can be delivered by means of a simple eye dropper-capped bottle or by means of a plastic bottle adapted to deliver liquid contents dropwise by means of a specially shaped closure.

Pharmaceutical compositions of this invention suitable for parenteral administrations comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

It has been found that diketopiperazines suitable for use in the present invention are present in some commercially-available intravenous pharmaceutical compositions containing albumin, immunoglobulin and erythropoietin. The diketopiperazines present in these pharmaceutical preparations are formed by the heating steps often used in the manufacture of these pharmaceutical compositions. The heating results in cleavage and cyclization of the two N-terminal and/or two C-terminal amino acids of the proteins to form diketopiperazines.

Accordingly, diketopiperazines for use in the present invention can be prepared by heating solutions of albumin, immunoglobulin, erythropoietin and other proteins and peptides. For example, a solution of albumin, immunoglobulin, erythropoietin or another protein or peptide in phosphate buffer at neutral pH is prepared. Preferably, the solution is a concentrated solution (e.g., about 100-500 mM) to achieve protonation of the N-terminal and/or C-terminal amino acid. The solution is heated at 60° C. for from about 2 hours to several days, preferably about 4 days, to cause formation of the diketopiperazines. Denaturation of the protein should, preferably, be avoided. This can be accomplished by using shorter times and/or by adding caprylic acid or N-acetyl tryptophan at about 0.02 M for each.

Diketopiperazines for use in the present invention can also be prepared by contacting a solution of albumin, immunoglobulin, erythropoietin or another protein or peptide with an enzyme that can cleave the two N-terminal amino acids from the protein or peptide (e.g., dipeptidyl peptidases) or an enzyme that can cleave the two C-terminal amino acids from the protein or peptide (e.g., carboxypeptidases). Suitable dipeptidyl peptidases and carboxypeptidases are available commercially from, e.g., Sigma. The reaction should be conducted at pH 6-8, preferably in a buffer, such as phosphate buffer, at a temperature high enough to speed the reaction but not so high that the protein is denatured (e.g., 37° C.).

The amino acid sequences of numerous proteins and peptides are known, and a protein or peptide with the desired N-terminal and/or C-terminal sequence can be chosen to give the desired diketopiperazine(s) using either method. Also, peptides with a desired sequence can be synthesized by well known methods and used.

The diketopiperazines can be purified from solutions containing them, including from the commercially-available pharmaceutical compositions comprising albumin, immunoglobulin and erythropoietin, by well known methods, such as size-exclusion chromatography (e.g., CENTRICON™ filtration), affinity chromatography (e.g., using a column of beads having attached thereto an antibody or antibodies directed to the desired diketopiperazine(s) or an antibody or antibodies directed to the truncated protein or peptide), anion exchange or cation exchange. The purified diketopiperazines can be used and incorporated into pharmaceutical compositions as described above.

Instead of purifying the diketopiperazines, pharmaceutical compositions comprising albumin, immunoglobulin, erythropoietin and/or other proteins and/or peptides normally found in the animal recipient can be administered for treatment of a T-cell mediated disease and can be used to inhibit T-cell activation. Although compositions comprising these proteins and/or peptides which are currently available commercially can be used if they contain diketopiperazines, it is highly preferred to treat the albumin, immunoglobulin, erythropoietin and/or other proteins and/or peptides as described above to increase the content of the desired diketopiperzine(s) before administration of the thus improved compositions. The animal is preferably a human, and the proteins and/or peptides are preferably human proteins and/or peptides. Oral administration of the composition(s) is preferred.

Effective dosage amounts of the protein and/or peptide compositions can be determined empirically, and making such determinations is within the skill of the art. In particular, to determine an effective dosage amount of a protein and/or peptide composition, the quantity of one or more diketopiperazines present in the composition can be measured, and an amount of the composition sufficient to deliver an effective amount of the diketopiperazine(s) can be administered to the animal. It is understood by those skilled in the art that the dosage amount will vary with the particular composition employed, the disease or condition to be treated, the severity of the disease or condition, the route(s) of administration, the rate of excretion, the duration of the treatment, the identify of any other drugs being administered to the animal, the age, size and species of the animal, and like factors known in the medical and veterinary arts. In general, a suitable daily dose of a protein and/or peptide composition will be that amount which is the lowest dose effective to produce a therapeutic effect. However, the daily dosage will be determined by an attending physician or veterinarian within the scope of sound medical judgment. If desired, the effective daily dose may be administered as two, three, four, five, six or more sub-doses, administered separately at appropriate intervals throughout the day. Administration should be continued until an acceptable response is achieved.

As noted above, it has been found that diketopiperazines are found in commercially-available intravenous pharmaceutical compositions of albumin, immunoglobulin and erythropoietin where manufacture of these compositions involves one or more heating steps (e.g., for sterilization). Diketopiperazines are also probably present in other pharmaceutical compositions of proteins and peptides where manufacture of the compositions involves heating steps. As described herein, many diketopiperazines have the ability to inhibit T-cell activation. Thus, it may not be desirable to administer compositions of albumin, immunoglobulin, erythropoietin or other proteins or peptides containing diketopiperazines to patients in many situations. For instance, albumin is often administered to patients suffering from trauma, immunoglobulin is often administered to patients suffering from infections or immune deficiencies, and erythropoietin is administered to anemic cancer or chronically ill patients whose immune systems are often compromised. Accordingly, the invention provides a method of removing at least some, preferably substantially all, of the diketopiperazines from such compositions. The diketopiperazines may be removed as described above (e.g., by size-exclusion chromatography (e.g., CENTRICON™ filtration), affinity chromatography (e.g., using a column of beads having attached thereto an antibody or antibodies directed to the desired diketopiperazine(s) or an antibody or antibodies directed to the albumin, immunoglobulin, erythropoietin or other protein or peptide), anion exchange or cation exchange) to produce improved compositions of albumin, immunoglobulin, erythropoietin and other proteins and peptides.

EXAMPLES

Example 1

Absorption of Asp Ala DKP (DA-DKP) and Glu Ala DKP (EA-DKP) from Rat Intestine

The rat intestine from the pyloric sphincter to the rectum was marginally isolated and perfused via the mesenteric artery with an erythrocyte based perfusate containing bovine serum albumin. The effluent perfusate from the gut was collected by cannulation of the portal vein and re-circulated (after re-oxygenation). After an equilibration period, a solution (approximately 1 ml) containing approximately 1 mg of Asp-Ala diketopiperazine (DA-DKP) or 1.4 mg of Glu-Ala diketopiperazine (EA-DKP) was administered by injection into the lumen of the duodenum.

After dosing, serial samples of the perfusate were collected at timed intervals up to 2 hours past dosing. Those samples were centrifuged and the plasmas assayed for both cyclic dipeptides by tandem liquid chromatography mass spectrometry (LC-MS).

The results showed that, after only 2 hours perfusion, the amounts of DA-DKP and EA-DKP which had been absorbed from the gut lumen into the circulation corresponded to 95% and 100% (actually 112%), respectively, of the dose administered.

Thus, both cyclic peptides are absorbed rapidly and efficiently from the gut lumen into blood, with no evidence of metabolism during transport across the gut wall. Hence these potential therapeutics may be given by mouth.

The rapid absorption of unchanged DA-DKP and EA-DKP from the gastrointestinal track into the blood combined with the lack of first pass hepatic clearance of both compounds in the isolated perfused rat liver (data not shown) shows that pre-systemic clearance is low. Consequently oral dosing will be an ideal route of administration.

Moreover, studies with isolated perfused rat kidney showed that, unlike many straight chain peptides, which are extensively metabolized by renal peptidases, the renal clearance of both cyclic dipeptides is relatively slow.

Collectively this data suggests that a dosing regimen of low daily doses of diketopiperazines is likely to be adequate for therapeutic purposes.

Preliminary pharmacokinetic data in rats after oral administration were consistent with the above for both cyclic dipeptides, with $T_{max}$ values of 30-60 minutes and $C_{max}$ values of 4-6 μg/ml (DA-DKP) and 0.6-1.1 μg/ml (EA-DKP) after oral dosing at 1.1-3.7 mg/kg body weight (DA-DKP) and 1.5-4.8 mg/kg body weight (EA-DKP) ($T_{max}$ is the time when the concentration reaches a maximum, and $C_{max}$ is the maximum concentration reached; both were calculated from a curve fit equation for the data obtained).

Preliminary data suggest that DA-DKP and other diketopiperazines cross the blood-brain barrier. Thus, DA-DKP and other diketopiperazines of the invention should be useful for treating nervous system disorders, such as multiple sclerosis.

Example 2

Inhibition of Human T-Lymphocyte Cytokine Production In Vitro by Fractions of Human Colostrum Containing Met-Arg DKP (MR-DKP) and by Asp-Ala DKP (DA-DKP)

A. Materials

This example demonstrates that DA-DKP, human colostrum (HC 2626) containing MR-DKP, and a low-molecular weight fraction of human colostrum (HC RBL; a fraction of human colostrum containing components of molecular weights less than 3000 prepared by passing de-fatted colostrum through an ultrafiltration membrane (CENTRICON™ filtration) to retain protein components larger than the molecular weight cutoff) also containing MR-DKP, inhibited human T-lymphocyte cytokine production. DA-DKP and MR-DKP were obtained from DMI Synthesis, Ltd., Cardiff, UK. These two diketopiperazines are small naturally-occurring compounds generated during the physiological response to inflammation. They are also sometimes found in human intravenous immunoglobulin (IVIg), human albumin and other biological preparations.

B. Inhibition of T-Cell Cytokine Production

Two different CD4-positive human T-lymphocyte clones were tested. One of the cell lines (TRiPS) was isolated from an influenza-immunized donor and is specific for hemagglutinin peptide 307-319. The other cell line (H4#9.25) was isolated from the autopsy brain tissue of a multiple sclerosis donor and is specific for myelin basic protein (amino acids 87-99). Both T-lymphocyte clones produce interleukin 8 (IL-8), IL-16, interferon-gamma (IFN-γ) and tumor necrosis factor alpha (TNF-α) after in vitro stimulation with either (1) specific antigen plus HLA-DR2-positive presenting cells or (2) anti-CD3 plus anti-CD28 antibodies.

The T-lymphocyte cell lines were stimulated for passage using approximately $4 \times 10^5$ cells on day 18-20 after a previous stimulation. Cells were washed once in cold Iscove's Modified Dulbecco Minimal Essential Medium (IMDM, Sigma) plus 10% fetal bovine serum (FBS; American Type Culture Collection (ATCC)) and resuspended in 1.0 ml cold IMDM medium containing a 1:500 dilution of anti-CD3 monoclonal antibody OKT3 (prepared from mouse ascites fluid). Cells were incubated with antibody for 30 minutes on ice, then washed with cold medium without FBS and combined with approximately $2 \times 10^6$ 4000R-irradiated normal human donor peripheral blood leukocytes (PBL), as feeder cells, in medium plus 50 U/ml human IL-2 (Xenometrix). Cultures were expanded by the addition of fresh IMDM medium with FBS plus IL-2 on day 3. Day of culture is measured from the day of stimulation with OKT3. Cells can be used for experiments starting on day 7 (at maximum proliferation), typically on day 14 (most sensitive to re-stimulation) and up until day 21 (resting cells approaching senescence).

Activation experiments were performed by withdrawing an aliquot of cells and washing twice with warmed (37° C.) IMDM medium. For each specific assay, $2 \times 10^5$ viable cells were pre-incubated in a total volume of 0.9 ml warmed IMDM medium containing the specified amount of treatment additive (e.g., HC 2626, DA-DKP, PMA, etc.) for 15 minutes at 37° C. An aliquot of $2 \times 10^5$ CD3/CD28 Dynabeads (Dynal), as activating stimulus, in 0.1 ml warmed IMDM was then added and the cultures incubated overnight (18 hours) at 37° C. Supernatants of the cell cultures were harvested after pelleting the cells by centrifugation. Cytokine content was assayed by specific ELISA (e.g., TNFα, IFNγ, IL-8, IL-16; Endogen).

Figure 2:
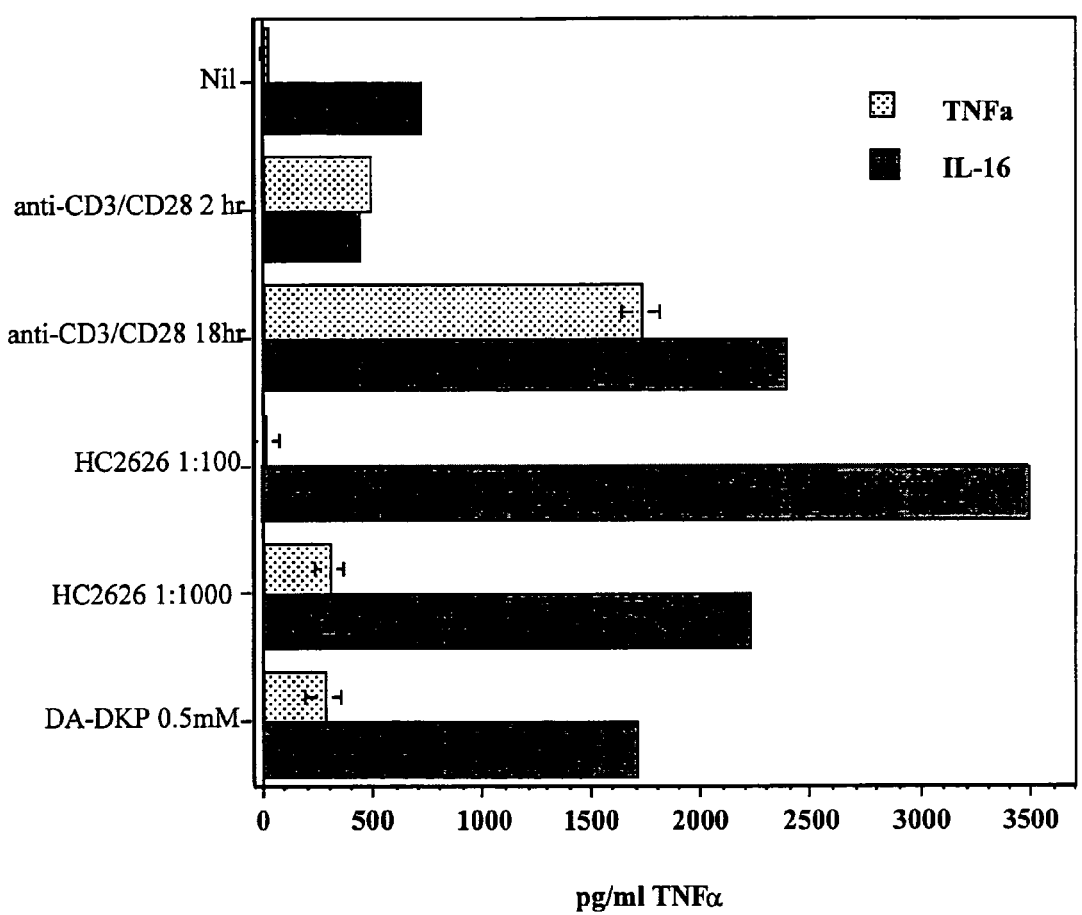
FIG. 2. Bar graph showing inhibition of secretion of tumor necrosis factor α (TNFα) and IL-16 from TriPS cells 12 days after stimulation with anti-CD3 OKT3 antibody. Indicates the inhibition of both TNFα and IL-16 secretion by human colostrum (HC) 2626 (containing MR-DKP) band DA-DKP. The maximal release observed using HC 2626 at 1:100 and 1:1000 dilutions is due to the lytic effect of high concentrations of human colostrum. No lysis is observed using 0.5 mM DA-DKP, and TNFα and IL-16 secretion are decreased.
Figure 3:
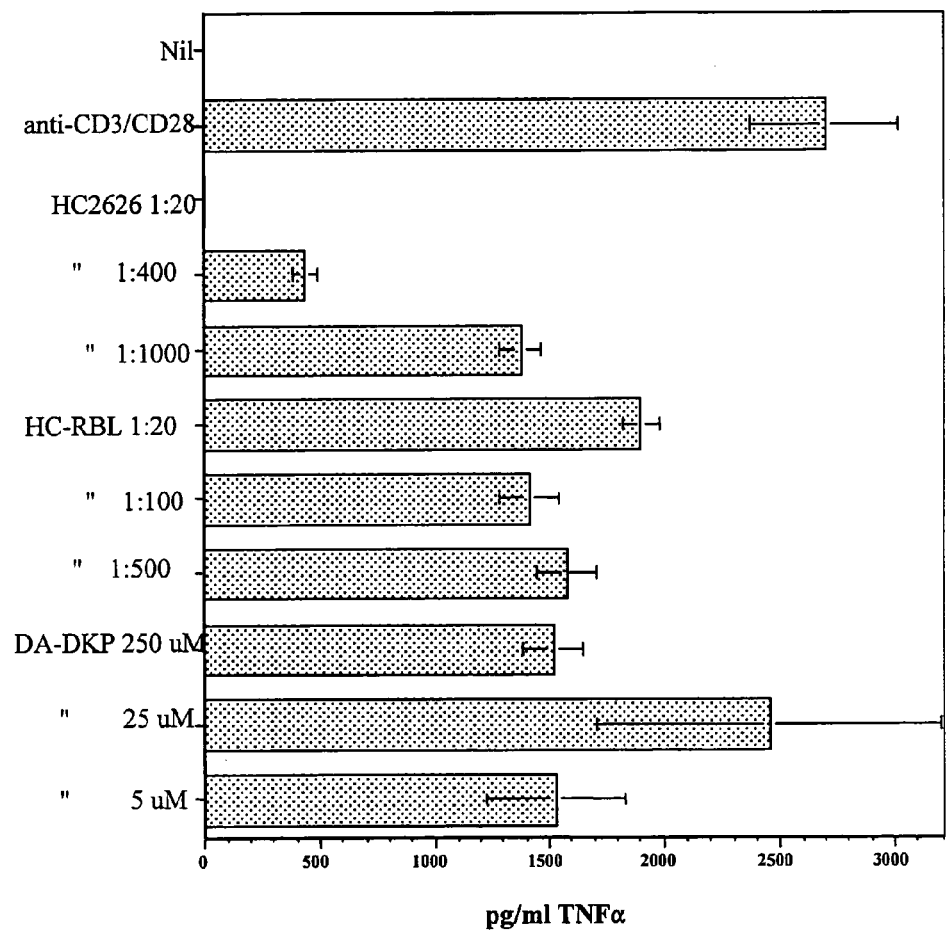
FIG. 3. Bar graph showing inhibition of TNFα secretion from TriPS cells 10 days after stimulation with anti-CD3 OKT3 antibody. Indicates that HC RBL and DA-DKP need to be investigated further for titratable response as seen with HC 2626. May indicated a potent activity.
Figure 4:
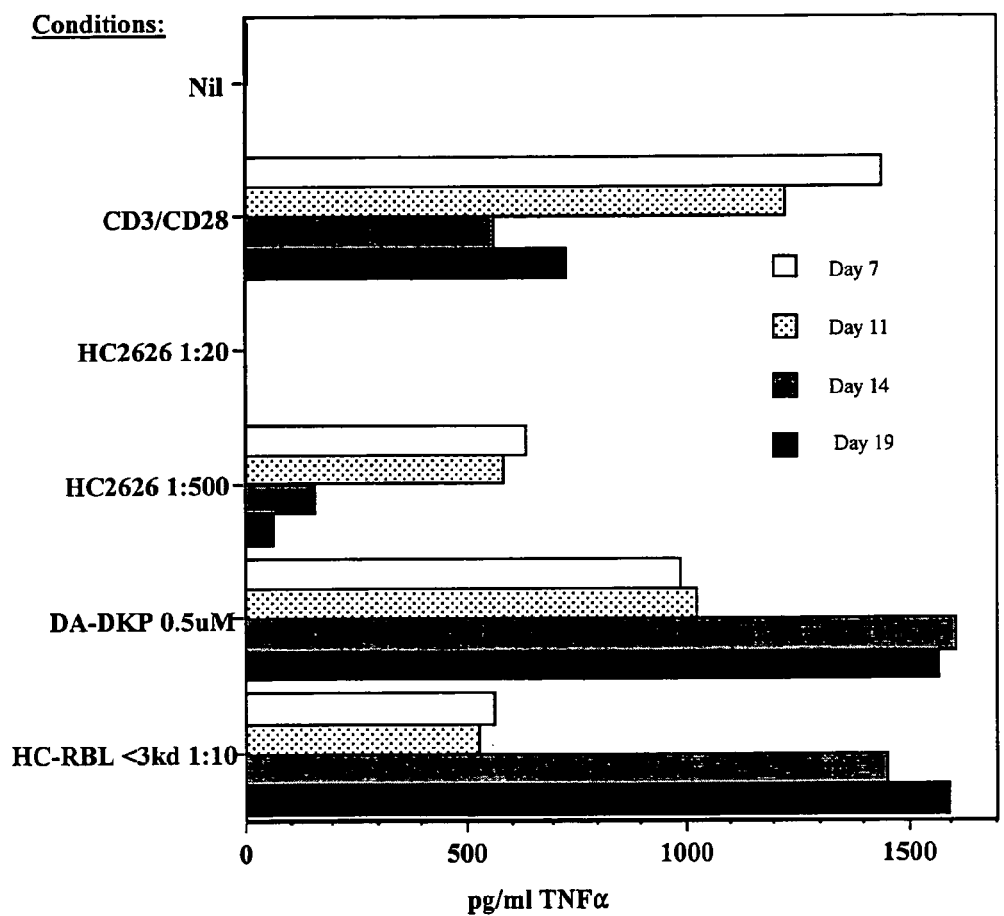
FIG. 4. Bar graph showing inhibition of TNFα secretion from TriPS cells at varying times after stimulation with anti-CD3 OKT3 antibody. Indicates that early in the stimulation cycle, the effect of DA-DKP and HC RBL is inhibitory, while later in the cycle (day 14) the effect is stimulatory. HC 2626 inhibits at all times, presumably due to other constituents.
Figure 5:
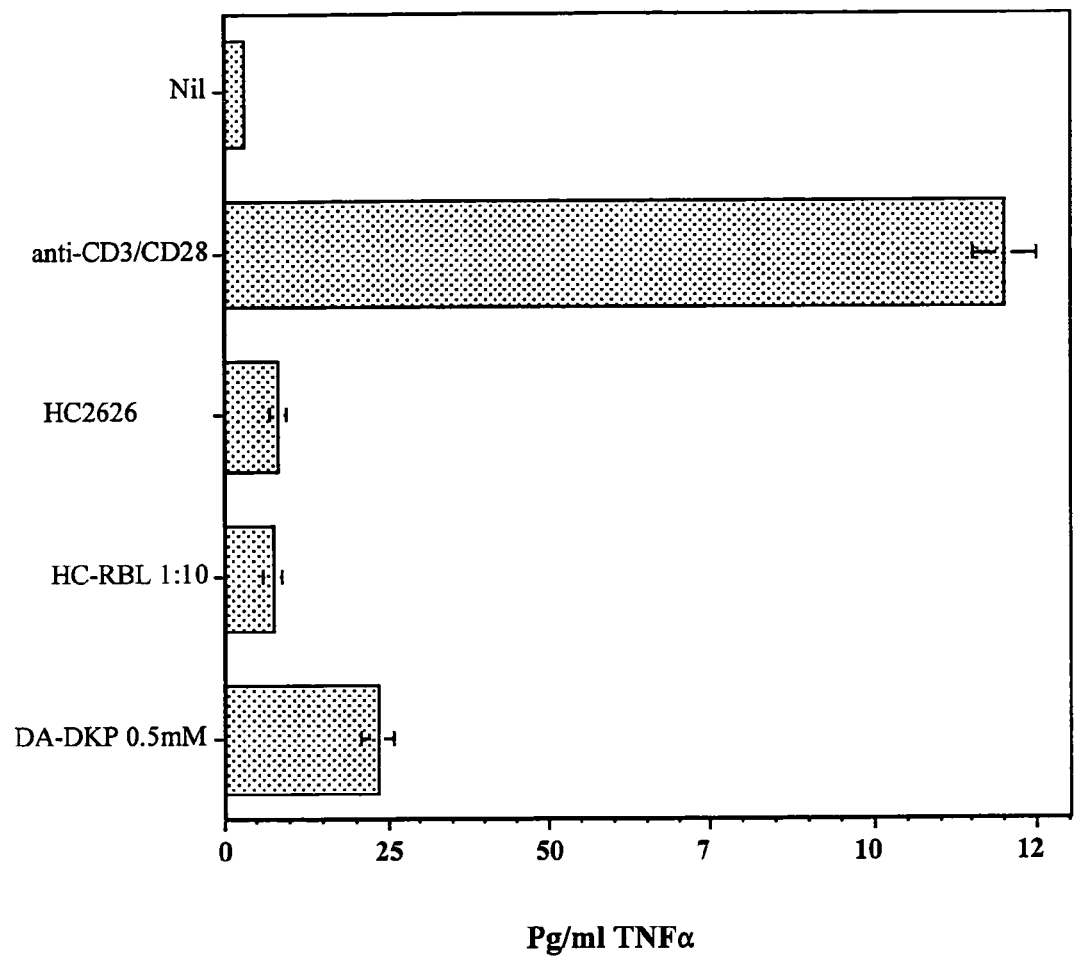
FIG. 5. Bar graph showing inhibition of TNFα secretion from H4#9.25 cells (CD4+ T-cell line isolated from autopsy brain tissue of a multiple sclerosis patient which is specific for myelin basic protein) on day 7-10 after stimulation with anti-CD3 OKT3 antibody. Indicates that TNFα secretion from this T-cell line is also inhibited by HC 2626, HC RBL and DA-DKP.

As shown in FIGS. 1-5, human colostrum (HC 2626) inhibited the in vitro cytokine production by both of the T-lymphocyte cell lines in a dose-dependent manner. As also shown in FIGS. 1-5, HC RBL and DA-DKP inhibited the in vitro cytokine production by both of the T-cell lines in a dose-dependent manner early in the stimulatory cycle. However, the effects of HC RBL and DA-DKP later in the cycle (day 14 or later) were stimulatory (see FIG. 4). HC 2626 and HC RBL both contain MR-DKP (as determined by mass spectrometry), but HC 2626 contains other constituents (including caseins that are relatively dephosphorylated proteins which may, therefore, be anti-inflammatory, as described in co-pending application Ser. No. 10/723,247, filed Nov. 25, 2003) besides MR-DKP which may be responsible for its inhibitory effects later in the cell cycle. Accordingly, HC RBL and HC 2626 (both containing MR-DKP), MR-DKP and DA-DKP should be useful in down-modulating the inflammatory cytokine response in T-cell-mediated and/or autoimmune diseases, such as multiple sclerosis, since they all inhibit cytokine production by T-cells early in the stimulatory cycle. These results also suggest that HC RBL, HC 2626, MR-DKP and DA-DKP will selectively affect antigen-specific T-cells without affecting resting T-cells.

C. Mechanism of Action

The mechanism of action of DA-DKP and HC 2626 (containing MR-DKP) was investigated. To do so, $1\times10^6$ day 18 TRiPS cells were incubated for 30 minutes at 37° C., either with nothing added ("Nil"), with CD3/CD28 Dynabeads added (CD3/CD28 beads), with CD3/CD28 beads and 0.5 mM DA-DKP, or with CD3/CD28 beads and 1:500 dilution of HC 2626 added. After the incubation, the cells were lysed in Cell-Lytic Mammalian Cell Extraction Reagent (Sigma).

The cell extracts were then separately incubated with duplicate Hypromatrix Arrays for 2 hours at room temperature, followed by two washes following the manufacturer's (Hypromatrix) protocol. The Hypromatrix Array is a nylon membrane blotted with antibodies to the transcription factors listed in Table 1 (custom manufactured by Hypromatrix). An antibody cocktail specific for phosphorylated-tyrosine, phosphorylated-serine and phosphorylated-threonine (Zymed) was added, incubated for 1 hour. Then, an anti-immunoglobulin antibody labeled with biotin was added. After washing the anti-immunoglobulin-biotin away, streptavidin-peroxidase was added, and the arrays given a final wash before adding a peroxidase-reactive luminescent substrate.

The results were visualized by exposure to film and scored as 0 (negative) or + to ++++ (positive) as presented in Table 2. As shown in Table 2, some cytokine transcriptional factor activation (ERK1/2) and release of pre-formed cytokines were inhibited by HC 2626 (containing MR-DKP) and DA-DKP.

TABLE 1

HYPROMATRIX ARRAY (CUSTOM): PROTEINS FOR PHOSPHORYLATION

| NUMBER | ACRONYM | COMPOUND |
|---|---|---|
| 1 | Akt 1/2 | protein kinase B, anti-apoptotic kinase |
| 2 | c-Cbl | TcR inhibitory pathway; $Tyr^{292}$ POation activates binding and inactivation of Syk and ZAP-70 |
| 3 | CBP | csk-binding protein (PAG); integral membrane protein transiently (and at low level) Tyr-de-POated to release csk |
| 4 | CREB | cAMP response element binding protein; POated (unk) to activate/down-reg IL-2 promoter |
| 5 | csk | COOH-terminal src kinase; $Ser^{364}$-POated, also Tyr-POated (activity?) - POates and inactivates lck |
| 6 | ERK1 | extracellular signal-related kinase |
| 7 | c-fos | AP-1 constituent activated by TcR stimulation; POated at both N- and C-unk residues |
| 8 | NFATC | nuclear factor of activated T-cells; intact in anergy |

TABLE 1-continued

HYPROMATRIX ARRAY (CUSTOM): PROTEINS FOR PHOSPHORYLATION

| NUMBER | ACRONYM | COMPOUND |
|---|---|---|
| 9 | c-jun | AP-1 constituent activated by TcR activation; POated by JNK-MAPK at $Ser^{63}$ |
| 10 | IκB-α | inhibitor of NFκB |
| 11 | pIκB-α | Ser-POated and inactivated NFκB inhibitor |
| 12 | p38 MAPK | mitogen-activated protein kinase |
| 13 | pI3 kinase/p85 | activated by glucocorticoids and β2-adrenergic-R |
| 14 | pten | cytoplasmic 3'-inositol phosphatase; tumor suppressor gene antagonizes PI 3'kinase by converting PI-PO back to inactive forms |
| 15 | c-Raf-1 | |
| 16 | Rap1 | negative TcR regulatory GTPase |
| 17 | Ras | kinase; inactivated during anergy |
| 18 | fyn | cell membrane-bound immediate TcR signal kinase |
| 19 | lck | cell membrane-bound immediate TcR signal kinase, active form is $Tyr^{395}$ POated; inactivated by csk POation at C-term Tyr |
| 20 | ZAP70kinase | signaller from CD3ζ; POated at ? by lck/fyn, ZAP70 POates LAT (linker for activation of T-cells) at Tyr's and Tyr's on SLP-76 |

TABLE 2

RESULTS

| COMPOUND | NIL | CD3/CD28 | DKP | HC2626 |
|---|---|---|---|---|
| Akt 1/2 | + | ++ | +++ | ++ |
| c-Cbl | — | — | — | — |
| CBP | + | ++ | ++ | ++ |
| CREB | — | — | — | — |
| csk | + | ++ | + | + |
| ERK1 | + | + | + | + |
| c-fos | — | — | — | — |
| NFATC | — | — | — | — |
| c-jun | ++ | + | + | + |
| IκB-α | ++ | ++ | + | + |
| pIκB-α | — | — | — | — |
| p38 MAPK | ++ | +++ | +++ | +++ |
| pI3 kinase/p85 | + | ++ | + | ++ |
| pten | — | — | — | — |
| c-Raf-1 | — | — | — | — |
| Rap1 | + | ++ | ++ | + |
| Ras | — | — | — | — |
| fyn | + | + | + | + |
| lck | — | — | — | — |
| ZAP70kinase | — | — | — | — |

Example 3

Inhibition of Human T Lymphocyte Cytokine Production In Vitro by Gly-Leu DKP (GL-DKP) and Ala-Pro DKP (AP-DKP)

GL-DKP and AP-DKP (obtained from DMI Synthesis, Ltd., Cardiff, UK) were tested as described in Example 2 using TRiPS and H4#9.25 cell lines. GL-DKP and AP-DKP were found to inhibit the in vitro cytokine production by both of these T-lymphocyte cell lines in a dose-dependent manner. The mechanism of action is currently under investigation as described in Example 2, and both cytokine transcriptional factor activation and release of pre-formed cytokine appear to be affected.

Example 4

Inhibition of Human T Lymphocyte Cytokine Production In Vitro by Asp Ala DKP (DA-DKP) and Tyr Glu DKP (YE-DKP)

Normal human lymphocytes were isolated from the peripheral blood of a normal human donor with Histopaque (Sigma). Then, 3-4×10$^5$ of the lymphocytes were suspended in 1 ml of IMDM medium without serum. The cells were stimulated with by adding 25 µl of a 1:2000 dilution of anti-CD3 antibody (Pharmingen, San Diego, Calif.) and incubating for 18 hours at 37° C.

Then, one of three DKP preparations and dexamethasone (final concentration of 10$^{-5}$ M) were added to triplicate cultures. The three DKP preparations were:

1. DA-DKP (obtained from DMI Synthesis, Ltd., Cardiff, UK; final concentration of 25 µg/ml in the cultures).

2. DKP-ZLB, a 25% albumin preparation (obtained from ZLB Bioplasma, AG 3000 Berne 22 Switzerland) heated for 4 days at 60° C., after which it was found to contain 0.5 mM DA-DKP, as determined by mass spectrometry (final concentration of 14 µg/ml DA-DKP in the cultures).

3. DKP-γ-glob—a γ-globulin preparation (obtained from Sigma, number G-4386) containing 12 mg/ml γ-globulin in phosphate-buffered saline, pH 7.4, was filtered through an ultrafiltration membrane (CENTRICON™ 3000) to retain protein components larger than the molecular weight cutoff, and the filtrate (containing components having MW less than 3000) was used. The filtrate contained a mass of 292, which is the mass of Tyr-Glu DKP (YE-DKP), as determined by anion exchange HPLC coupled to negative electrospray mass spectrometry. The filtrate was used at a 1:4 final dilution in the cultures.

After addition of the DKP preparations or dexamethasone, the cultures were incubated for 18 hours at 37° C. Then, the amounts of IL-2, IFNγ and TNFα released into each culture were measured by ELISA (Pierce Biotechnology, Rockford, Ill. 61105).

The results are presented in Table 3 below. As can be seen, the greatest reduction of release of all three cytokines was obtained with DKP-γ-glob. Flow cytometry looking at the number of CD69+ T-cells (CD69 is a marker found on activated T-cells) also showed that DKP-γ-glob reduced the number of CD69+ T-cells by about 90%, as compared to a reduction of about 50% by dexamethasone, despite the internalization of T-cell receptor complex.

TABLE 3

| Stimulation | Treatment | U/ml IL-2 | pg/ml IFNγ | pg/ml TNFα |
|---|---|---|---|---|
| Nil | — | 0.24 ± 0.1 | 2.3 ± 0.9 | 2.8 ± 0.5 |
| CD3 | — | 2.6 ± 0.5 | 289 ± 35 | 98 ± 3.2 |
| CD3 | DA-DKP | 1.4 ± 0.3 | 306 ± 17 | 74 ± 4.7 |
| CD3 | DKP-ZLB | 1.4 ± 0.4 | 311 ± 18 | 130 ± 2.9 |
| CD3 | DKP-γ-glob | 0.24 ± 0.25 (91% reduction) | 2.1 ± 0.1 (99% reduction) | 1.6 ± 0.6 (98% reduction) |
| CD3 | Dexamethasone | 0.9 ± 0.1 (65% reduction) | 76 ± 7.32 (74% reduction) | 4.1 ± 0.3 (96% reduction) |

We claim:

1. A method of reducing the symptoms, severity or both of inflammation or an inflammatory disease involving, caused by or exacerbated by T-cells, comprising administering to an animal in need thereof an effective amount of a pharmaceutical composition comprising a filtrate of a solution of a protein or peptide, wherein the filtrate is produced by passing the solution of a protein or peptide over an ultrafiltration membrane with a molecular weight cutoff that retains a protein selected from the group consisting of albumin, immunoglobulin and erythropoietin, and wherein the filtrate comprises: a diketopiperazine selected from the group consisting of YE-DKP, MR-DKP and DA-DKP.

2. The method of claim 1 wherein the filtrate contains components having molecular weights less than 3000.

3. The method of claim 1 wherein the protein or peptide is a human protein or peptide.

4. The method of claim 1 wherein the protein or peptide is a human albumin.

5. The method of claim 2 wherein the protein or peptide is a human protein or peptide.

6. The method of claim 2 wherein the protein or peptide is a human albumin.

7. The method of claim 1 wherein the animal is a human.

8. A method of reducing the symptoms, severity or both of a T-cell mediated disease, comprising administering to an animal in need thereof an effective amount of a pharmaceutical composition comprising a filtrate of a solution of a protein or peptide, wherein the filtrate is produced by passing the solution of a protein or peptide over an ultrafiltration membrane with a molecular weight cutoff that retains a protein selected from the group consisting of albumin, immunoglobulin and erythropoietin, and wherein the filtrate comprises: a diketopiperazine selected from the group consisting of YE-DKP, MR-DKP and DA-DKP.

9. The method of claim 8 wherein the filtrate contains components having molecular weights less than 3000.

10. The method of claim 8 wherein the protein or peptide is a human protein or peptide.

11. The method of claim 8 wherein the protein or peptide is a human albumin.

12. The method of claim 9 wherein the protein or peptide is a human protein or peptide.

13. The method of claim 9 wherein the protein or peptide is a human albumin.

14. The method of claim 8 wherein the animal is a human.

15. The method of claim 8 wherein the T-cell mediated disease is graft rejection, graft versus host disease, an unwanted delayed-type hypersensitivity reaction, a T-cell mediated pulmonary disease or an autoimmune disease.

16. The method of claim 8 wherein the T-cell mediated disease is multiple sclerosis, neuritis, polymyositis, psoriasis, vitiligo, Sjogren's syndrome, rheumatoid arthritis, Type 1 diabetes, autoimmune pancreatitis, inflammatory bowel diseases, Crohn's disease, ulcerative colitis, celiac disease, glomerulonephritis, scleroderma, sarcoidosis, autoimmune thyroid diseases, Hashimoto's thyroiditis, Graves disease, myasthenia gravis, Addison's disease, autoimmune uveoretinitis, pemphigus vulgaris, primary biliary cirrhosis, pernicious anemia, or systemic lupus erythematosis.

17. The method of claim 8 wherein the T-cell mediated disease is pulmonary fibrosis or idiopathic pulmonary fibrosis.

18. A method of reducing the symptoms, severity or both of inflammation or an inflammatory disease involving, caused by or exacerbated by T-cells, comprising administering to an animal in need thereof an effective amount of a pharmaceutical composition comprising an alanine-aspartic acid diketopiperazine (DA-DKP) and a component selected from the group consisting of caprylic acid, N-acetyl tryptophan and combinations thereof, wherein the pharmaceutical composition is produced by passing a solution of albumin over an ultrafiltration membrane with a molecular weight cutoff that retains albumin, and wherein the filtrate comprises the DA-DKP.

19. The method of claim 18, wherein the pharmaceutical composition filtrate contains components having molecular weights less than 3000.

20. The composition of claim 18, wherein the albumin is a human albumin.

21. A method of reducing the symptoms, severity or both of a T-cell mediated disease, comprising administering to an animal in need thereof an effective amount of a pharmaceutical composition comprising an alanine-aspartic acid diketopiperazine (DA-DKP) and a component selected from the group consisting of caprylic acid, N-acetyl tryptophan and combinations thereof,
wherein the pharmaceutical composition is produced by passing a solution of albumin over an ultrafiltration membrane with a molecular weight cutoff that retains albumin, and wherein the filtrate comprises the DA-DKP.

22. The method of claim 21, wherein the pharmaceutical composition filtrate contains components having molecular weights less than 3000.

23. The composition of claim 21, wherein the albumin is a human albumin.

24. The composition of claim 18, wherein the composition is an isotonic aqueous solution.

25. The composition of claim 21, wherein the composition is an isotonic aqueous solution.

* * * * *